(12) United States Patent
Betremieux-Merlier et al.

(10) Patent No.: US 12,241,894 B2
(45) Date of Patent: Mar. 4, 2025

(54) IN VITRO DIAGNOSIS DEVICE COMPRISING BEADS AND USES THEREOF

(71) Applicant: DIAGAST, Loos (FR)

(72) Inventors: Christine Betremieux-Merlier, Wattignies (FR); Laziza Amniai, Lille (FR); Julien Schelpe, Gondecourt (FR)

(73) Assignee: DIAGAST, Loos (FR)

( * ) Notice: Subject to any disclaimer, the term of this patent is extended or adjusted under 35 U.S.C. 154(b) by 1093 days.

(21) Appl. No.: 16/969,208

(22) PCT Filed: Feb. 15, 2019

(86) PCT No.: PCT/EP2019/053886
§ 371 (c)(1),
(2) Date: Aug. 12, 2020

(87) PCT Pub. No.: WO2019/158726
PCT Pub. Date: Aug. 22, 2019

(65) Prior Publication Data
US 2020/0408749 A1    Dec. 31, 2020

(30) Foreign Application Priority Data

Feb. 16, 2018  (EP) .................................... 18305164

(51) Int. Cl.
*G01N 33/543* (2006.01)
*G01N 33/538* (2006.01)
*G01N 33/68* (2006.01)

(52) U.S. Cl.
CPC ....... *G01N 33/5436* (2013.01); *G01N 33/538* (2013.01); *G01N 33/6854* (2013.01)

(58) Field of Classification Search
CPC .................. G01N 33/5436; G01N 33/538
See application file for complete search history.

(56) References Cited

U.S. PATENT DOCUMENTS

| 5,552,276 A | 9/1996 | Mochida et al. |
| 5,905,028 A | 5/1999 | Frame et al. |

(Continued)

FOREIGN PATENT DOCUMENTS

| CA | 1312265 C | 1/1993 |
| EP | 0334015 A2 | 9/1989 |

(Continued)

OTHER PUBLICATIONS

Deng et al., *Developments and new applications of UV-induced surface graft polymerizations*, 34 Progress in Polymer Science 156-193 (2009).

(Continued)

*Primary Examiner* — Natalia Levkovich
(74) *Attorney, Agent, or Firm* — Panitch Schwarze Belisario & Nadel LLP; Erin M. Dunston

(57) ABSTRACT

The present invention relates to an in-vitro diagnosis device for detecting and/or identifying antigen and/or antibody from a sample of biological fluid, particularly from a sample of blood or sample of blood components. The invention also relates to different uses of this device such as the detection and/or the identification of red blood cells antigens, platelet antigens, viral antigens, bacterial antigens, parasite antigens, the detection and/or the identification of anti-red blood cells antibodies, antiplatelet antibodies, antiviral antibodies, antibacterial antibodies and antiparasitic antibodies.

15 Claims, 22 Drawing Sheets

1a

1b

(56) References Cited

U.S. PATENT DOCUMENTS

| | | | |
|---|---|---|---|
| 7,432,111 B2 | 10/2008 | Cho et al. | |
| 2015/0140579 A1* | 5/2015 | Chaibi | G01N 33/80 435/7.25 |
| 2016/0327507 A1* | 11/2016 | Davis | G01N 33/48721 |

FOREIGN PATENT DOCUMENTS

| | | |
|---|---|---|
| JP | H08-054390 A | 2/1996 |
| JP | 2001-502795 A | 2/2001 |
| RU | 2398235 | 10/2009 |
| WO | WO-95/31731 A1 | 11/1995 |
| WO | WO-98/16831 A1 | 4/1998 |
| WO | WO-02/052263 A1 | 7/2002 |
| WO | WO-03/016902 A1 | 2/2003 |
| WO | WO-2005/005986 A1 | 1/2005 |
| WO | WO-2005/036123 A2 | 4/2005 |
| WO | WO 2007/135571 | 11/2007 |
| WO | WO-2008/148886 A1 | 12/2008 |
| WO | WO-2009/007649 A2 | 1/2009 |
| WO | WO-2012/010666 A1 | 1/2012 |

OTHER PUBLICATIONS

Houngkamhang et al., *ABO Blood-Typing Using an Antibody Array Technique Based on Surface Plasmon Resonance Imaging*, 13 Sensors 11913-11922 (2013).

International Search Report and Written Opinion issued in International Application No. PCT/EP2019/053886 (Mar. 14, 2019).

Manavi et al., *The sensitivity of syphilis assays in detecting different stages of early syphilis*, 17 International Journal of STD & AIDS 768-771 (2006).

Mujahid et al., *Blood Group Typing: From Classical Strategies to the Application of Synthetic Antibodies Generated by Molecular Imprinting*, 16(51) Sensors 1-17 (2016).

Perraut et al., *Standardization of a Multiplex Magnetic Bead-based for Simultaneous Detection of IgG to Plasmodium Antigens*, 4(2) Journal of Immunological Techniques in Infection Diseases 1-8 (2015).

Pipatpanukul et al., *Rh blood phenotyping (D, E, e, C, c) microarrays using multichannel surface plasmon resonance imaging*, 102 Biosensors and Bioelectronics 267-275 (2018).

Porcelijn et al., *A new bead-based human platelet antigen antibodies detection assay versus the monoclonal antibody immobilization of platelet antigens assay*, 54 Transfusion 1486-1492 (2014).

Robertson et al., *Detection of circulating parasite antigen and specific antibody in* Toxocara canis *infections*, 74 Clin. Exp. Immunol. 236-241 (1998).

Souza-Atta et al., *Detection of specific IgE antibodies in parasite diseases*, 32 Brazilian Journal of Medical and Biological Research 1101-1105 (1999).

Van den Hurk et al., *A Review of Membrane-Based Biosensors for Pathogen Detection*, 15 Sensors 14045-14078 (2015).

Wong et al., *Rapid detection of antibodies in sera using multiplexed self-assembling bead arrays*, 350 Journal of Immunological Methods 171-182 (2009).

Xu et al., *Quantitative and multiplexed detection for blood typing based on quantum dot-magnetic bead assay*, 12 International Journal of Nanomedicine 3347-3356 (2017).

Yang et al., *Micro flow cytometry utilizing a magnetic bead-based immunoassay for rapid virus detection*, 24 Biosensors and Bioelectronics 855-862 (2008).

Zhai et al., *A robust, portable and backflow-free micromixing device based on both capillary- and vacuum-driven flows*, 18 Lab Chip 276-284 (2018).

Chua et al., *A rapid DNA biosensor for the molecular diagnosis of infectious disease*, 26 Biosensor and Bioelectronics 3825-3831 (2011).

\* cited by examiner a b a b c
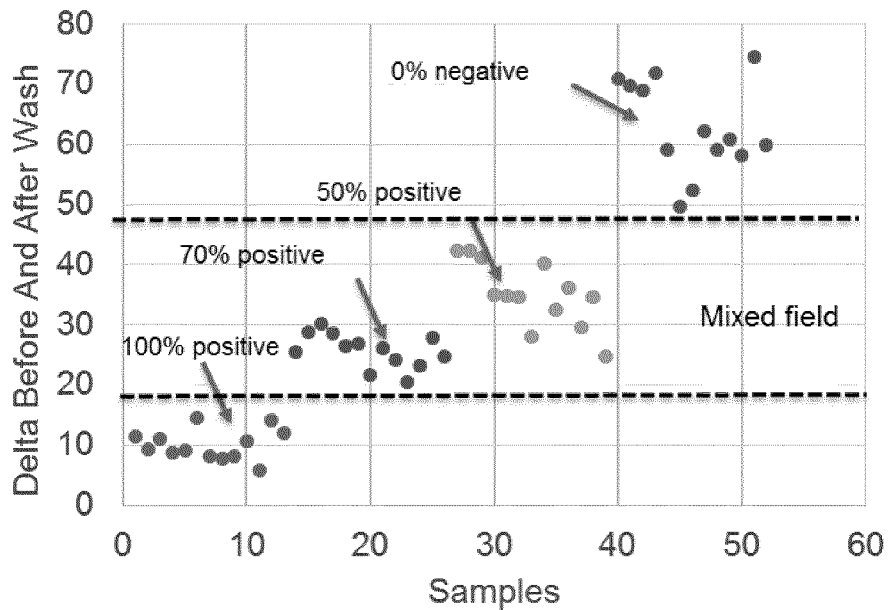
d
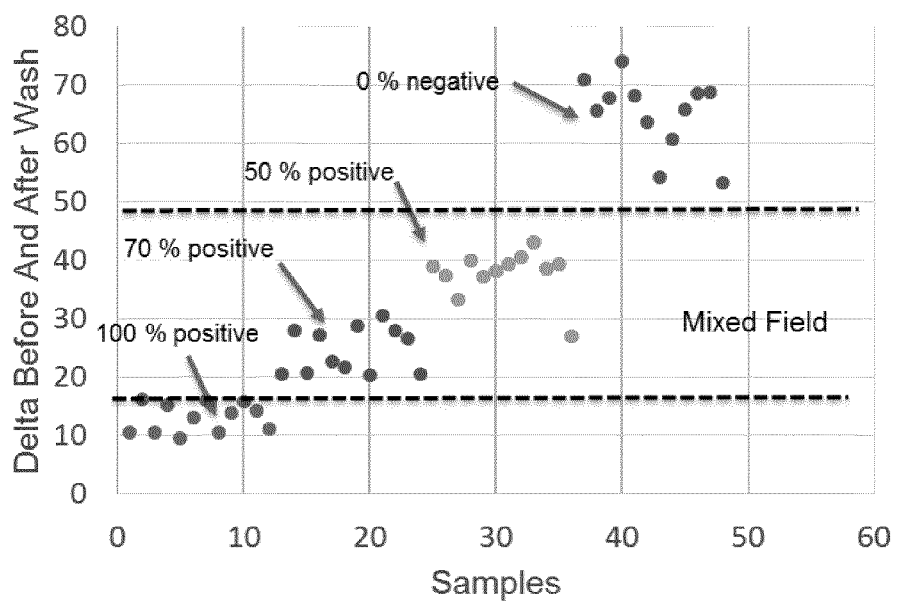
Figure 12 (followed)

a

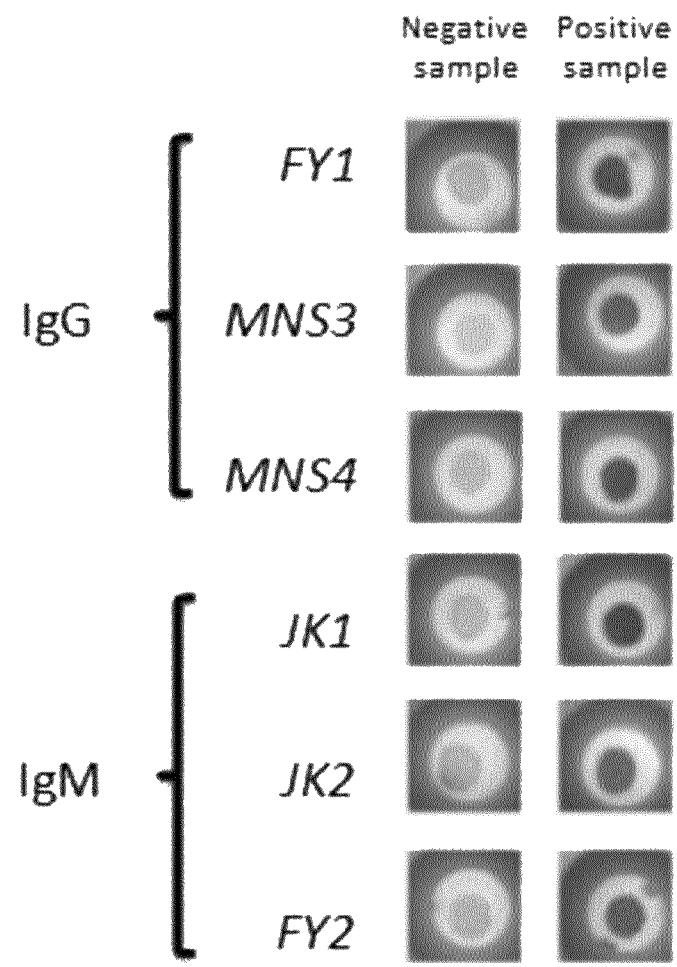
Figure 13 (followed)

a b

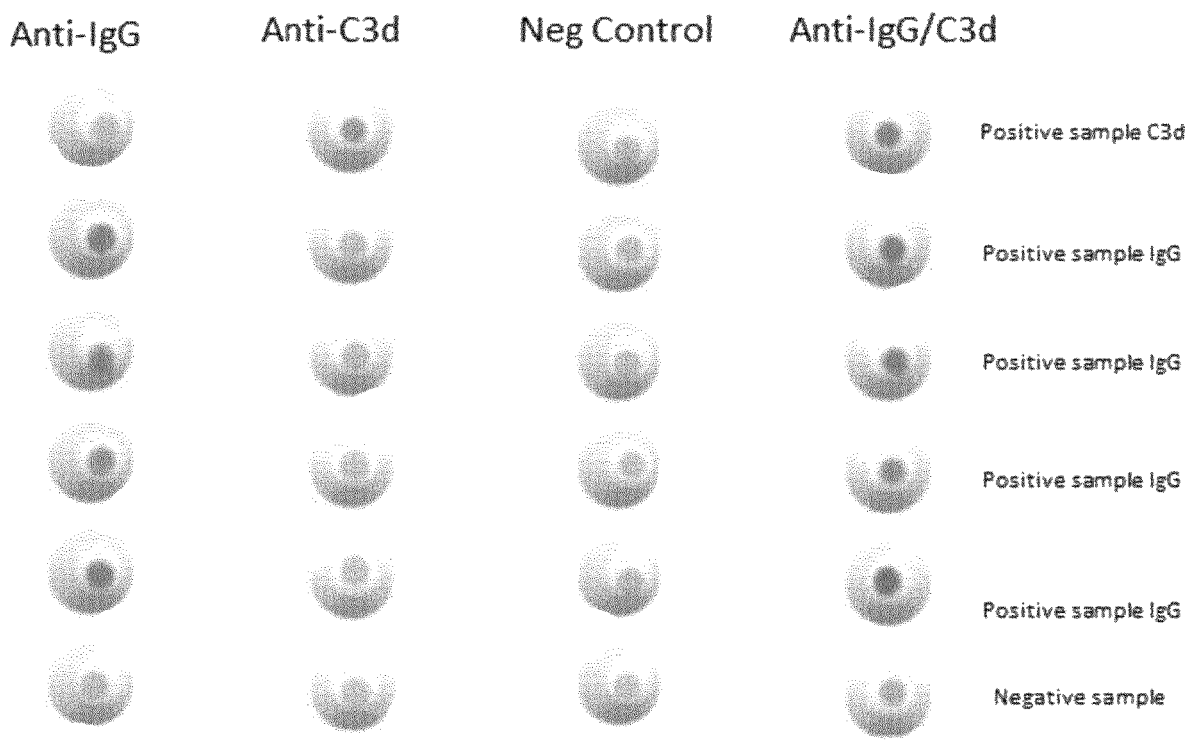
Figure 15 (followed)

a b c

Figure 16 (followed)

a b

IN VITRO DIAGNOSIS DEVICE COMPRISING BEADS AND USES THEREOF

CROSS-REFERENCE TO RELATED APPLICATIONS

This application is a U.S. National Stage Application pursuant to 35 U.S.C. § 371 of International Patent Application PCT/EP2019/053886, filed on Feb. 15, 2019, and published as WO 2019/158726 on Aug. 22, 2019, which claims priority to European Patent Application 18305164.8, filed on Feb. 16, 2018, all of which are incorporated herein by reference in their entireties for all purposes.

FIELD OF THE INVENTION

The present invention is in the field of immune diagnosis. Particularly, the present invention relates to an in vitro diagnosis device for detecting and/or identifying antigen and/or antibody from a sample of biological fluid, particularly from a sample of blood or sample of blood components. The invention also relates to various uses of this device such as the detection and/or the identification of red blood cells antigens or anti-red blood cells antibodies, platelet antigens or antiplatelet antibodies, viral antigens or antiviral antibodies, bacterial antigens or antibacterial antibodies, parasite antigens or antiparasitic antibodies. In vitro methods using the device of the invention are also a part of the present invention.

BACKGROUND OF THE INVENTION

Immunodiagnostic assays are methods that are available in several formats of test and usable to detect antibodies, antigens or combination of both. Commonly, these detection tests are based on the use of immobilized antigens which capture any present specific antibody in the tested sample whereas the tests used to detect antigens consist on immobilized antibodies that allow the capture of the specific antigen that is present in the sample.

These assays are widely used for example in immunohematology, for detecting infectious pathogens etc . . . , especially to ensure blood transfusion safety.

Blood transfusion consists in an intravenous injection of concentrated red cell preparations (globular concentrates) obtained from donor blood. There are two major risks in blood transfusion:

The principal risk is the possibility of bringing together an antibody and its erythrocyte antigen in the recipient's body (person receiving the transfusion). The consequences of such an immunological reaction may range from inefficient transfusion with no clinical sign, to a slight clinical reaction (anxiety, shivers), serious clinical reaction (shock, hemoglobinurea, renal failure) or dramatic clinical reaction (shock, disseminated intravascular hemolysis) resulting in death.

Blood transfusion is a possible source of disease transmission. A myriad of agents can potentially be transmitted through blood transfusions, including bacteria, viruses, and parasites. Of these, bacteria are the most commonly transmitted and include species of genus *Treponema, Yersinia, Proteus, Pseudomonas, Escherichia, Klebsiella, Acinetobacter,* and *Serratia*, while among gram-positive organisms, *Propionibacterium, Staphylococcus, Bacillus, Clostridium,* and *Enterococcus* were isolated. Viral agents that are capable of being transmitted through blood transfusion include Human immunodeficiency virus (HIV), Hepatitis viruses, West Nile virus (WNV), Cytomegalovirus (CMV), Human T-cell lymphotrophic viruses (HTLVs) and Parvovirus B19. Another example is Protozoal organisms that include species of the genus *Plasmodium*, which cause malaria and that can be passed on through transfusion.

To ensure blood transfusion safety, it is required, on the one hand, that donor red blood cells are said to be compatible with the recipient's blood if the recipient has no circulating antibodies directed against the donor's erythrocyte antigens and, on the other hand, that donor red cells are free from transfusion-transmissible infectious agents.

To ensure compatibility between the donor red blood cells and the recipients, tests for determining the blood groups and the presence of anti-red blood cells antibodies in the plasma/serum are currently used.

The aim of immuno-haematological diagnosis is to determine and/or identify a immune reaction between a red blood cells antigen and an antibody specifically directed against such antigen. For this, it is necessary to have tools for determining antigens present at the surface of the red blood cells. Their presence or their absence defines the blood group. It is also possible to identify whether recipient's blood contains one or more antibodies directed against the known antigens of the donor's red blood cells, the presence of an antibody meaning the possibility of incompatibility.

Among all the antigenic variants of an erythrocyte membrane antigen constituting blood groups, over thirty erythrocyte antigen systems have been identified in humans to date: the ABO system with A (ABO1), B (ABO2), AB (ABO3) and A1 (ABO4), the Rh system with D (RH1), E (RH3) ore (RH5) and C (RH2) or c (RH4) antigens, the Kell system (K or KEL1, k or KEL2, . . . ), the Duffy system (Fya or FY1, Fyb or FY2, . . . ), the Kidd system (Jka or JK1, Jkb or JK2, . . . ), the MNS (MNS1, MNS2, MNS3, MNS4 . . . ) system or other systems less frequently investigated in practice which also exist such as Lutheran, Lewis, etc. Individuals with the same combination of erythrocyte antigens belong to the same erythrocyte blood group. Blood groups become even more complex and numerous when several antigen systems are used.

Customary techniques consist in searching for and identifying the presence or absence of red blood cells antigens at the surface of these cells and/or searching for and identifying the presence or the absence of anti-red blood cells antibodies of blood group in the plasma or in the serum.

For example, for the ABO system, the Beth-Vincent test determines antigens carried by the red blood cells, and the complementary Simonin-Michon test or reverse blood grouping determines antibodies circulating in the serum or in the plasma.

In the Beth-Vincent test, the red blood cells of the individual are brought together with reagents of antibodies of known specificity. Generally, this test is made visible by observation of agglutination of red blood cells when the reagents of antibodies recognise the corresponding red blood cells antigens.

In the Simonin-Michon test, the plasma or serum of the individual is brought together with red blood cells tests each belonging to a precise antigenic group of the ABO system. This is a test of agglutination of red blood cells from the antibodies present in plasma or serum of the individual. These antibodies which are IgM-type immunoglobulins are able to agglutinate red blood cells in vitro. They are called "regular" antibodies since they are systematically present in the serum or plasma of individuals who do not carry the corresponding antigen at the surface of their red blood cells.

A second class of antibodies called "irregular" (or "immune") antibodies also exists. Their presence in the serum or plasma is optional and they are directed against antigens of the non-ABO systems. This generally involves IgG (sometimes IgM), appearing during antigen stimulation by foreign red blood cells, for example following an immunization against one or more antigens after a blood transfusion or during pregnancy by a maternal immune reaction directed against foetal erythrocyte antigens not belonging to the maternal blood group, or after an allograft.

The screening of these irregular antibodies is called indirect agglutinin test (IAT) or indirect Coombs assay. This test is used to detect the presence or the absence of IgG antibodies directed against various red blood cells antigens, in an individual's blood using a human antiglobulin to facilitate agglutination since IgG, by itself, is not able to spontaneously induce agglutination in vitro. For this, the test aims to demonstrate the binding of these antibodies on test red blood cells of known antigenicity. This method is carried out simultaneously on several red blood cells with different known antigenicity and the comparison of the results makes possible to identify the specificity of the IgG present.

The risk is greater for the most immunogenic antigens, such as Rh D (RH1), but also for other rhesus types (E (RH3)>c (RH4)>e (RH5)>C (RH3)), the antigen of the Kell system (KEL1), the antigens of the Duffy system (FY1, FY2), the antigens of the Kidd system (JK1, JK2), etc . . . .

In practice, it is not possible to take into consideration all these antigens when carrying out a transfusion, as obtaining the right blood group at the right moment would not be possible, especially as some antigenic combinations are extremely rare. Standard transfusions only take into account the ABO group and the presence of absence of the antigen D (RH:1 or RH:−1). In situations when there is the presence of irregular antibodies, a number of other systems are taken into consideration, notably Rh System (C (RH2) or c (RH4) and E (RH3) or e (RH5)) and Kell system, and at times other systems. Therefore, for these risk situations, it is important to ensure the compatibility between the donor's blood group and the recipient's blood group by taking into account the presence or risk of occurrence of these irregular anti-red blood cells antibodies.

Thus, in recipient patients with irregular anti-red blood cells antibodies or in a risk situation, such as patients receiving multiple transfusions, it is of importance to select erythrocyte concentrate units which are transfused in such a way that the donor's red blood cells are devoid of antigens against which the recipient's antibodies are directed or likely to appear.

Tests to determine the blood groups and to search and identify irregular anti-red blood cells are mandatory in these patients and it is used preventively in all recipient patients prior to an administration of erythrocyte concentrates and in pregnant women to detect potential feto-maternal incompatibility. Additional tests by means of a direct compatibility test with the donor's red blood cells in the presence of recipient serum or plasma are also mandatory used to confirm the compatibility. In these cases, neither agglutination reaction nor lysis reaction in the techniques used in IAT should be found.

Searching for so-called irregular antibodies entails detecting the presence or absence in the blood of an individual of immunoglobulins directed against various red blood cells antigens. When the antibodies are already fixed in vivo the direct test or direct Coombs assay is performed. In the case of alloantibody search, the aim is to reveal the fixing of these immunoglobulins on red blood tests whereof the antigens are known, with the indirect Coombs' technique.

There is a large number of processes and devices used for detecting and/or identifying the red blood cells antigens and for detecting and/or identifying the anti-red blood cells antibodies in the field of immuno-haematology, but they have many disadvantages.

The slide method consists in mixing, on a glass slide or white porcelain support, a drop of donor or recipient blood with anti-A (anti-ABO1), anti-B (anti-ABO2) and anti-D (anti-RH1), separately. The agglutination can be visually observed from which the ABO and Rh D systems of blood can be determined. The test is completed in 5-10 min and is inexpensive. However, it is an insensitive method. The test cannot be conducted for weakly or rarely reactive antigens from which the results are difficult to interpret, and additionally, a low titer of anti-A (anti-ABO1) or anti-B (anti-ABO2) could lead to false positive or false negative results. Due to its prompt results, it is very much valuable in emergency cases for preliminary blood group matching. However, it is not reliable enough to completely ensure safe transfusion.

The tube test consists of determining both Beth-Vincent and Simonin-Michon assays. In this method, for the Beth-Vincent grouping, blood cells are placed in two test tubes along with saline as a diluent media, and then one drop of each anti-A (anti-ABO1) and anti-B (anti-ABO2) is added separately in these samples. These tubes are subjected to centrifugation for a few min, and then, the resultant matrix is gently shaken for observing agglutination. The purpose of centrifugation is to ensure enhanced chemical interactions, particularly for weaker antibodies to react, thus leading to agglutination. In a similar fashion, Simonin-Michon reverse grouping can be performed by treating the blood serum against red blood cells reagent groups of A1 and B (and optionally of blood groups O and A2), and the subsequent agglutination pattern is monitored. In general, the tube method is much more sensitive than the slide test and requires a low volume of reagents, and some unexpected antigens can also be detected. However, in infants, reverse grouping is somewhat difficult to perform, since they produce insufficient amounts of antibodies to be determined. Since this test is a manual method, its use for high throughput analysis is very limited.

Among classical methods, microplating technology consists of a large number of small tubes that contain a few microliter (μl) of reagents, which are treated against the blood samples. Following centrifugation and incubation, the subsequent agglutination can be examined by an automatic read out device. This method is more sensitive and fast analysis for blood typing and for detecting/identifying anti-red blood cells antibodies with low reagent volumes and the feasibility of automation for high throughput analysis. However, since microplating techniques need a centrifuging phase followed by an agitation step, there is therefore the risk of undoing weak agglutination without succeeding in resuspending strong agglutination. They must be carried out under visual check and particular attention must be paid to adherence phenomena of some reagents.

Filtration techniques by gel test is a standard procedure for quantifying cell agglutination. The column contains gel matrix to trap agglutinates. For blood typing, red blood cells are mixed with anti-A (anti-ABO1), anti-B (anti-ABO2) and anti-D (anti-RH1) reagents or other antibodies against other blood groups in microtubes under controlled incubation and centrifugation. For reverse blood typing and for detecting/identifying anti-red blood cells antibodies, plasma or serum are mixed with red blood cells with known antigenicity under controlled incubation and centrifugation. The gel particles trap the agglutinates, whereas non-agglutinated blood cells are allowed to pass through the column. The analysis time can be reduced by using glass beads in place of gel material, since in this way, faster centrifugation speeds can be achieved, which leads to rapid results. This technology is sensitive, straightforward and relatively easy to operate for less trained personnel. However, the main risk consists of not detecting some agglutinations especially during the plasmatic test of the ABO group due to dissociation by shearing forces of small agglutinates as they pass into the gel.

Also, there is a major disadvantage to all these techniques because they need centrifuging step to decant the red blood cells or have them pass through the gel, a restricting step which adds considerable time and analysis costs and which needs the use of bulky centrifuges which are difficult to handle.

Other methods based on Molecular Imprinting (for review: Mujahid, 2016, Sensors), on Antibody Array Technique surface by plasmon resonance imaging (Houngkamhang, 2013, sensors; Pipatpanukul, 2018, Biosensors and Bioelectronics), on quantum dot-magnetic bead assay (Xu, 2017, International Journal of Nanomedicine) or on In capillary- or vacuum-driven microfluidics (Zhai, 2017, Lab on a Chip) and other methods have also been described in the relating art.

WO 2012010666 describes magnetic immunodiagnostic methods for the determination of antibody/antigen complexes of blood group and phenotype The immunofiltration method, described for example in application EP2167967, consists of capturing an analyte present in a sample as it passes through a porous membrane carrying a capturing element and reveals its presence by a revelation element. This method has significant sensitivity and specificity problems, because when the sample is deposited it spreads and imbibes the porous membrane, and many analytes are lost in the dead volume of the porous membrane or pass outside the capture area. The same applies for the revelation solution. It is therefore necessary to oversize the absorption system to be able to deposit larger volumes of samples to be tested and revelation solution, preventing miniaturised tests from being performed, the kinetics of which are controlled, exempt from receiving revelation agents and utilisable with a robot pipette.

In an attempt to resolve this problem and concentrate the signal emitted following antigen/antibody reaction, it has been proposed in application CA1312265 or WO02052263 to interpose above and below the hydrophilic porous membrane a hydrophobic structure pierced to force the flow to pass through the capture spot. However, with these devices there is still the problem of centrifugal diffusion from a spot, and the revelation elements which pass through the capture spot and which are not fixed to it will be able to diffuse centrifugally in the hydrophilic porous membrane and be stored at the periphery of the spot.

Another major problem of existing immunofiltration devices today is control of the motion speed of the sample through the membrane and in some cases pre-incubation time. These times are important since interaction between the capturing element (often an antibody) and the analyte (often an antigen) as well as between the analyte and the revelation element has specific kinetics. Without a particular system, passing through a hydrophilic membrane is rapid (500 µl/min).

To control the flow, it has been proposed to utilise a piston, in particular in application US2008318342.

To control pre-incubation time, it has been proposed in application WO03016902 to use a device in two parts: an upper part comprising a sample collection area and a porous membrane, and a lower part comprising a porous membrane and an absorbent membrane.

Such mechanical approaches are difficult to execute using a robot since they need development and use of dedicated systems. They also expose professionals to any projections during handling.

Another method, described in EP0334015, consists in using an extra membrane subjacent to the first to control flow, but the proposed device fails to resolve the problems linked to diffusion of the sample and the revelation element in the hydrophilic porous membrane.

Platelet transfusion, also known as platelet concentrate, is used to prevent or treat bleeding in people with either a low platelet count or poor platelet function. Preventative transfusion is often done in those with platelet levels of less than $10 \times 10^9$/L. In those who are bleeding transfusion is typically carried out at less than $50 \times 10^9$/L. Platelet are given by injection into a vein. Platelets can be produced either from whole blood or by apheresis. To date, 33 human platelet alloantigens (HPAs) have been identified on six functionally important platelet glycoprotein (GP) complexes. The greatest number of recognized HPA (20 of 33) resides on the GPIIb/IIIa complex, which serves as the receptor for ligands important in mediating haemostasis and inflammation. These include HPA-1a, the most commonly implicated HPA in FNAIT and PTP in Caucasian populations. Other platelet GP complexes, GPIb/V/IX, GPIa/IIa and CD109, express the remaining 13 HPAs. Of the recognized HPAs, 12 occur as six serologically and genetically defined biallelic 'systems' where the "a" form designates the higher frequency allele and the "b" form, the lower. Twenty-one other HPAs are low-frequency or rare antigens for which postulated higher frequency "a" alleles have not yet been identified as antibody specificities. In addition to the HPA markers, platelets also express ABO and human leucocyte antigen (HLA) antigens. Blood group matching (ABO, RH1) is typically recommended before platelets are given.

Accurate typing of patients for HPA antigens is required in several different clinical situations and blood services need to maintain panels of HPA-typed apheresis-platelet donors and whole-blood donors to support HPA-alto-immunized patients. The value of serological HPA phenotyping is limited as often too few platelets can be obtained from thrombocytopenic patients, and reliable serotyping reagents for HPA antigens, other than HPA-1a and HPA-5b, are rare. In contrast to red blood cells phenotyping, with the exception of HPA-1a, no monoclonal antibodies have been developed for HPA typing. However, several methods have recently been published for rapid screening assays using either polyclonal or recombinant anti-HPA-1a. These phenotyping assays can complement genotyping assays for the provision of HPA-selected donor panels.

It is important to ensure compatibility between the platelets' donor and the platelets' recipient. However, unmatched platelets, however, are often used due to the unavailability of matched platelets. Incompatibility may result in allo-immune platelet disorders including foetal and neonatal alloimmune thrombocytopenia (FNAIT), posttransfusion purpura (PTP) and multi-transfusion platelet refractoriness (MPR)

FNAIT, often known as feto-maternal allo-immune thrombocytopenia (FMAIT), occurs as a consequence of maternal immunization against foetal platelet allo-antigens inherited from the father. Maternal IgG alloantibodies then cross the placenta and cause immune destruction of platelets in utero, a situation analogous to haemolytic disease of the newborn.

Post-transfusion Purpura (PTP) is a rare but severe disease that occurs approximately a week after transfusion of any blood product containing platelets or platelet membranes. The patients are presumably sensitized by previous pregnancy or transfusion and respond to a second challenge of incompatible platelets by making high-titre HPA (and often HLA) antibodies. The resulting immune destruction of transfused platelets may contribute to the transfusion reactions that commonly occur.

MPR is defined as an inadequate increment in the platelet count following transfusion of random ABO identical donor platelets. It is a common complication in patients receiving multiple platelet transfusions.

Although a wide range of techniques have been developed for HPA antibody detection over the last 25 years, four techniques, or modifications of them, have become the most common; (1) the platelet immunofluorescence test (PIFT); (2) monoclonal antibody immobilization of platelet antigens (MAIPA) assay; (3) the solid-phase red cell adherence assay; and (4) a variety of ELISA-based techniques. However, proficiency in anti-platelet antibody detection depends on a variety of factors, including techniques, cell panels and operator experience which may render some of the above-mentioned techniques costly, difficult to implement and less reliable.

To detect potential transfusion-transmissible infection, many diagnostic tests that exploit immune response have been developed during the last four decades. The most usually used tests are designed to detect either antigens of the infectious agents such as viral antigens, bacterial antigens and parasite antigens or to detect antibodies directed against the infectious agent produced by immunization upon infection. Nevertheless, these tests do not suit all the situations and every test has limits, which must be known and taken into account during its selection. Often the immunodiagnostic is based on the use of antibody as reagent.

There are different methods used in immunodiagnostics tests. Some of these methods are described below.

Immunoprecipitation is the simplest immunoassay method that measures the quantity of precipitate, which forms after the reagent antibody has incubated with the sample and reacted with its respective antigen to form an insoluble aggregate. Immunoprecipitation reactions may be qualitative or quantitative.

The particle immunoassays detect the presence of antibody or specific antigens in a sample that are tested using particles which are coated with either the antigen or the appropriate antibody. By linking several antibodies to the particle (gelatine or latex), the particle is able to bind many molecules simultaneously and facilitates agglutination. This greatly accelerates the speed of the visible reaction. The *Treponema pallidum* particle agglutination assay (also called TPPA test) is another example of particle immunoassays used for detecting antibodies against the causative agent of syphilis which is a possible transfusion-transmissible infection agent (Manavi et al. 2006 Int. J. STD AIDS). It is an indirect agglutination assay in which gelatine particles are sensitized with *T. pallidum* antigen. The particles aggregate to form clumps when the patient serum is positive for syphilis while a negative test shows no clumping of gelatine particles.

Immunonephelometric assay is another example of immunoassays developed for detection of infections. When the immune complexes formed by the union of antibody and antigen is too small to precipitate, these complexes can be measured using an instrument called a nephelometer because they will scatter incident light. The antigen concentration can be determined within min of the reaction.

Radioimmunoassay (RIA) uses radioactive isotopes to label either the antigen or antibody. This isotope emits gamma rays which are usually measured following removal of unbound radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme (EIA), fluorescent (FIA) or cheminulescence (CLIA) immunoassays.

EIA, FIA and CLIA are currently the most often used tests to detect viral, bacterial and parasite infections, especially the transfusion-transmissible infections in blood donor samples. One of the most widely used EIA methods for detection of infectious diseases is the enzyme-linked immunosorbent assay (ELISA). There are numerous patents and publications showing the performances of such assays for the detection of infectious agents.

These methods are similar in their principle and differ only by the mode of detection of the resulting immune complexes: colorimetric for the EIA and ELISA, and measurement of the fluorescence and the luminosity produced by a enzymatic/chemical reaction for FIA and CLIA. Fluorescence and chemiluminescence measurements are inherently more sensitive than colorimetric measurements. Therefore, these methods have greater analytical sensitivity than EIA methods, which employ optical density measurement.

It also exists fast/simple unit tests without intermediate stage and disposable, that are only once used and eliminated. Most of these tests are based on immunochromatography, in which the sample (blood, plasma or serum) passes through an inert strip and reacts with reagents (antibodies or antigens) that have been beforehand immobilized on this strip. Any positive reaction is visualized as a dot or a band appearing on the strip. These tests are easy to use and require no additional reagent, excepted those included in the kit. They also give a simple qualitative result within a few min. However, these tests are not suitable for the screening of large numbers of samples.

In order to overcome the above-disadvantages, the Applicant implemented an in vitro diagnosis device for detection, from a sample of blood or one of its components, of at least one reaction between an antigen and an antibody directed specifically against this antigen comprising a hydrophobic porous membrane wherein at least one hydrophilic reaction area intended to receive said sample, has a surface less important than the surface of the hydrophobic porous membrane. This device is described for example in patent application WO2013/186482. It remedies several disadvantages arising from the above-mentioned tests, particularly arising from immunofiltration tests by:
    preventing returns of revelation agent responsible for false positives
    heightened sensitivity from using lower volumes
    miniaturisation and automation of the system
    control of the kinetics of reactions without need for mechanical handling of the device.

Despite the evident advantages of this device, there is still a need to improve the sensitivity and specificity of the performed diagnostic when this diagnostic comprises the use of a capturing agent and when this capturing agent is an antibody (for the detection of a corresponding antigen in the sample) or an antigen (for the detection of a corresponding antibody in the sample). When using of said device part of the capturing agent (for example, antibodies against the blood cells antigens) disposed on the hydrophilized reaction area during the diagnosis test is adsorbed by the porous membrane with the solution used for antibodies dilution. Consequently, the specificity and the sensitivity of the test are reduced. To compensate this "loss" of capturing agent, it is necessary to add a big quantity of capturing agent which may increase the cost of this diagnosis test.

To overcome this drawback, the inventors of the present invention have tested several technical solutions such as the use of thicker porous membrane or of less porous membrane but without significant result.

Instead to investigate other possibility to modulate the characteristics of the porous membrane or the others structural elements of this device, the inventors surprisingly found that the addition of particularly selected beads on which surface the capturing agent (for example, an antibody or an antigen) may be fixed or adsorbed, deposed on the reaction area of the porous membrane, allows to retain the capturing agent on the surface of the membrane and thus improves the signal emitted when the capturing agent binds the analyte (for example, an antigen or an antibody). Consequently, the use of such beads allows to improve the specificity and the sensitivity of the previously disclosed device without using an important quantity of capturing agent.

The bead on which surface are fixed antibodies and/or antigens are well known in the art for diagnosis purpose. For example, international application WO 95/31731 discloses a method for detecting red blood cells antigens, said method comprising adding a sample containing blood cells in column containing particles on which surface are fixed specific anti-red blood cells antibodies via proteins ligands. However, the described method does not use a device comprising a hydrophilized porous membrane and does not deal with the problem relating to the absorption of the capturing agent through the membrane.

Thus, the association of partially hydrophilized porous membrane with beads on which surface are directly or indirectly fixed or adsorbed antibodies and/or antigens as capturing agent for performing in vitro diagnosis method having high specificity and sensitivity is surprising in the light of the state of the relating prior art.

SUMMARY OF THE INVENTION

As indicated above, in order to improve the sensitivity and the specificity of the detection and/or the identification of an antigen and/or an antibody and to reduce the quantity of used analytes, the inventors implemented a device similar to the one disclosed in the patent application WO2013/186482 which further comprises beads disposed on the reaction area, wherein antibodies and/or antigens are fixed or adsorbed on the bead surface.

According to one aspect, the present invention thus relates to an in-vitro diagnosis device for detecting and/or identifying an antigen and/or an antibody from a sample of biological fluid, preferably from a sample of blood or a sample of blood components, comprising:
a support, and
a hydrophobic porous membrane arranged in the support comprising at least one hydrophilic reaction area intended to receive said sample, the surface of the hydrophilic reaction area which is smaller than the surface of the hydrophobic porous membrane comprises at least one antibody and/or antigen, wherein said antibody and/or antigen is fixed or adsorbed on a bead surface.

The inventors of the present invention have performed several tests and have demonstrated that the in vitro diagnosis device of the invention may be used for detecting and/or identifying different types of antigens or antibodies. For that, different types of antibodies and/or antigens may be fixed or adsorbed on the bead surface. These antibodies may be selected from antibodies directed against red blood cells antigens, from antibodies directed against platelet antigens, antiviral antigens, anti-bacterial antigens and antiparasitic antigens or anti-immunoglobulins. These antigens may be selected from red blood cells antigens, platelet antigens, viral antigens, bacterial antigens and parasitic antigens.

According to another aspect, the present invention thus relates to a use of the in vitro device according to the invention for determining and/or identifying:
at least one antigen selected from the group comprising red blood cells antigens including a mixed-field population, platelet antigens, viral antigens, bacterial antigens and parasite antigens;
at least one antibody selected from the group comprising anti-red blood cells antibodies, antiplatelet antibodies, antiviral antibodies, antibacterial antibodies and antiparasitic antibodies
from a sample of biological fluids, preferably from a sample of blood or a sample of blood components.

The inventors have particularly demonstrated that the in vitro device of the present invention may be used in an in vitro method for detecting and/or identifying red blood cell antigens and/or in vivo-sensitized red blood cells and/or platelet antigens from a sample of biological fluids, particularly, from a sample of blood or blood components.

According to another aspect, the present invention thus relates to an in vitro method for detecting and/or identifying red blood cell antigens and/or in vivo-sensitized red blood cells and/or platelet antigens from a sample of blood or sample of blood components comprising the following steps:
adding a solution containing said sample on the reaction area of the in vitro device according to the invention,
reading before rinsing for sample loading control
depositing a rinse solution on the reaction area, and
determining the presence of said antigens or said blood cells by determining the presence of an antigen/antibody interaction if in the reaction area appears a red or a pink spot or determining the absence of said antigens or said blood cells by determining the absence of an antigen/antibody interaction if in the reaction area appears a colourless spot.

Moreover, the inventors have also demonstrated that the in vitro device of the present invention may be used in an in vitro method for detecting and/or identifying anti-red blood cells antibodies from a sample of biological fluid, particularly from a sample of blood or blood components.

Another aspect of the present invention thus relates to an in vitro method for detecting and or identifying anti-red blood cells antibodies from a sample of blood or a sample of blood components, comprising the following steps:
incubating the sample to be tested with a buffer and red blood cell tests of known antigenicity or incubating the recipient's plasma or serum with the donor's red blood cells,
depositing the mixture on the reaction area of the in vitro device according to the invention, depositing a rinse solution on the reaction area, and
determining the presence of anti-red blood cell antibodies by determining the presence of an interaction antibody/antigen if in the reaction area appears a red or pink spot or determining the absence of said antibodies by determining the absence of an interaction antibody/antigen if in the reaction area appears a colourless spot.

The in vitro device of the present invention may be used in an in vitro method for detecting and/or identifying antiplatelet antibodies from a sample of biological fluid, particularly from a sample of blood or blood components.

Another aspect of the present invention thus relates to an in vitro method for detecting and or identifying antiplatelet antibodies from a sample of blood or a sample of blood components, comprising the following steps:
incubating the sample to be tested with a buffer and platelet tests of known antigenicity or incubating the recipient's plasma or serum with the donor's platelets,
depositing the mixture on the reaction area of the in vitro device according to the invention,
depositing a rinse solution on the reaction area, and
determining the presence of antiplatelet antibodies by determining the presence of an interaction antibody/antigen if in the reaction area appears a red or pink spot or determining the absence of said antibodies by determining the absence of an interaction antibody/antigen if in the reaction area appears a colourless spot.

The in vitro device of the invention may be also used in an in vitro method for detecting and/or identifying different types of antigens selected from the group comprising viral antigens, bacterial antigens and parasite antigens or different types of antibodies selected from the group comprising antiviral antibodies, anti-bacterial antibodies and/or anti-parasitic antibodies, said antibodies being produced against viral, bacterial or parasite antigens upon infection.

Still another aspect of the present invention thus relates to an in vitro method for detecting and/or identifying antigens selected from the group comprising viral antigens, bacterial antigens and parasite antigens from a sample of biological fluid, preferably from a blood sample or a sample of blood components comprising the following steps:
optionally incubating the sample to be tested with a buffer,
adding a solution containing said sample or mixture of the sample with the buffer on the reaction area of the in vitro device according to the invention,
optionally reading before rinsing for sample load control;
optionally depositing a rinse solution on the reaction area, and
determining the presence of said antigen by determining the presence of an antigen/antibody interaction if in the reaction area appears colored spot or determining the absence of said antigen by determining the absence of an antigen/antibody reaction if in the reaction area appears a colourless spot.

According with another aspect, the present invention also refers to an in vitro method for detecting and/or identifying antibodies selected from the group comprising antiviral antibodies, anti-bacterial antibodies and/or antiparasitic antibodies from a sample of biological fluid, preferably from a blood sample or a sample of blood components comprising the following steps:
optionally incubating the sample to be tested with a buffer,
adding a solution containing said sample or mixture of the sample with the buffer on the reaction area of the in vitro device according to the invention,
optionally reading before rinsing for sample load control;
optionally depositing a rinse solution on the reaction area, and
determining the presence of said antigen by determining the presence of an antigen/antibody interaction if in the reaction area appears colored spot or determining the absence of said antigen by determining the absence of an antigen/antibody reaction if in the reaction area appears a colourless spot.

The characteristics and advantages of the present invention will emerge from the following detailed description, from the examples demonstrating some embodiments of the invention also showed in the set of figures annexed to the application.

DETAILED DESCRIPTION OF THE INVENTION

Unless defined otherwise, all technical and scientific terms used herein have the same meaning as commonly understood by one of ordinary skill in the art to which this invention belongs. Some of these definitions are mentioned in the Background part of the present application and are applied to the present invention. Specific definitions are also given in the detailed description below.

In Vitro Device of the Invention

As indicated above, the inventors of the present invention have implemented an in vitro device for determining and/or identifying with high specificity and sensitivity an antigen and/or an antibody.

In one aspect the in vitro device of the present invention is an in vitro diagnosis device for detecting and/or identifying an antigen and/or antibody, from a sample of biological fluid, preferably from a sample of blood or a sample of blood components comprising:
a support, and
a hydrophobic porous membrane arranged in said support comprising at least one hydrophilic reaction area intended to receive said sample, the surface of the hydrophilic reaction area which is smaller than the surface of the hydrophobic porous membrane comprises at least one antibody and/or antigen, wherein said antibody and/or antigen is fixed or adsorbed on a bead surface.

The device of the present invention is suitable for detecting and/or identifying several types of antigens or antibodies. This detection and/or identification is performed via the antigen binding to the antibody fixed on adsorbed on the bead surface or via the antibody binding to the antigen fixed or adsorbed on the bead surface. In this context, any antibody and/or antigen may be fixed or adsorbed on the bead surface in the device of the present invention depending on the type of antigen or the antibody to be detected and/or identified. The in vitro device of the invention is thus not only for detecting and/or for identifying specific antigens or antibodies (as red blood cells antigens and anti-red blood cells antibodies) but may be adapted for the detection and/or for the identification of different types of antigens and antibodies. The person skilled in the art will be able to adapt the in vitro device of the present invention depending on antibody or antigen of interest to be detected and/or identified by fixing on the bead surface an antigen or an antibody linking the antibody or the antigen of interest respectively.

Consequently, the term "antibody" is used herein in the broadest sense and specifically covers monoclonal antibodies (including full length monoclonal antibodies) of any isotype such as IgG, IgM, IgA, IgD, and IgE, polyclonal antibodies, multispecific antibodies, chimeric antibodies, and antigen-binding fragments. An antibody reactive with a specific antigen can be generated by recombinant methods such as selection of libraries of recombinant antibodies in phage or similar vectors, or by immunizing an animal with the antigen or an antigen-encoding nucleic acid.

A typical antibody is comprised of two identical light chains and two identical heavy chains that are joined by disulfide bonds. In the meaning of the invention, the term "light chain" refers to mammalian immunoglobulin light chain, lambda (λ) or kappa (κ), having two successive domains: one constant domain and one variable domain.

The term "heavy chain" refers to chain of mammalian immunoglobulin denoted by: α, δ, ε, γ, and μ. Within these five classes, immunoglobulins can be also distributed in subclasses (IgG1, 2, 3 or 4, IGA1 or 2) according to the heavy chain (γ1, γ2, γ3, γ4, α1 and α2). Each heavy chain has two regions, the constant region and the variable region. The constant region is identical in all antibodies of the same isotype. The variable region of each heavy chain is composed of a single Ig domain.

The "variable region" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. Each variable region contains three segments called "complementarity-determining regions" ("CDRs") or "hypervariable regions", which are primarily responsible for binding an epitope of an antigen. The CDRs thus direct the specificity of the binding of the antibody. They are usually referred to as CDR1, CDR2, and CDR3, numbered sequentially from the N-terminus. The most highly conserved portions of the variable regions are called the "framework regions".

In one embodiment of the present invention, the antibodies used in the invention, particularly the antibodies fixed or adsorbed on the bead surface are polyclonal antibodies. A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

According to another embodiment, the antibodies used in the invention, particularly the antibodies fixed or adsorbed on the bead surface are monoclonal antibodies.

As used herein, the term "monoclonal antibody" refers to an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody population arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen.

A "chimeric antibody", as used herein, is an antibody in which the constant region, or a portion thereof, is altered, replaced, or exchanged, so that the variable region is linked to a constant region of a different species, or belonging to another antibody class or subclass.

A "antigen-binding fragments", as used herein, is a region on an antibody that binds to antigens. It is composed of one constant and one variable domain of each the heavy and the light chain.

According to one preferred embodiment of the present invention, the antibodies are selected from the group comprising anti-red blood cells antibodies, antiplatelets antibodies, antibodies directed against viral antigens, antibodies directed against bacterial antigens and antibodies directed against parasite antigens, preferably from the anti-red blood cells antibodies or antiplatelets antibodies.

As used herein, the term "antiplatelets antibodies" or "antibodies of platelet antigens" relates to one or more antibodies directed against one or more platelets antigens. Preferably, the antibodies of platelet antigens used in the present invention can be a purified or semi-purified monoclonal antibody, a purified or semi-purified polyclonal antibody or an antiserum.

As used herein the term "antibodies directed against viral antigens" relates to one or more antibodies directed against a viral antigen, said antibodies being produced upon an infection of a subject. Preferably, the antibodies against viral antigens used in the present invention can be a purified or semi-purified monoclonal antibody, a purified or semi-purified polyclonal antibody or an antiserum. The antiviral antibodies detected and/or identified by the in vitro device of the present invention maybe selected from the group comprising antibodies against antigens specific to Chikungunya, Cytomegalovirus, Dengue, Ebola, EBV, Encephalitis, Feline Leukemia Virus, Hantavirus, Hepatitis A, Hepatitis B, Hepatitis C, Hepatitis D, Hepatitis E, Herpes, HIV, HTLV, Influenza Lassa, Measles, Mumps, Norovirus, Papillomavirus, Parvovirus, Rubella, SARS, Varicella, West Nile virus and Zika. Particularly, the detection of antibodies directed against HIV, HTLV Hepatitis B or Hepatitis C is mandatory for blood transfusion safety. Particularly, the in vitro device of the present invention is used for detecting and/or identifying HIV, Hepatitis B and Hepatitis C, more particularly Hepatitis B.

As used herein the term "antibodies directed against bacterial antigens" relates to one or more antibodies directed against a bacterial antigen that are produced upon an infection of the subject. Preferably, the antibodies against bacterial antigens used in the present invention can be a purified or semi-purified monoclonal antibody, a purified or semi-purified polyclonal antibody or an antiserum. These antibodies may be polyclonal or monoclonal antibodies, particularly monoclonal antibacterial antibodies well known to person skilled In the art. For example such antibodies may be selected from Gram positive or Gram negative bacteria, particularly from *Borrelia, Chlamydia, Helicobacter Pylori, Mycoplasma, S. Typhi, Yersinia, Proteus, Pseudomonas, Escherichia, Klebsiella, Acinetobacter, Clostridium, Serratia, Propionibacterium, Staphylococcus, Bacillus, Treponema* and *Enterococcus*. Particularly, antibacterial antibody is directed against a specific antigen of *Treponema*, particularly *Treponema pallidum* which is responsible for syphilis.

As used herein the term "antibodies directed against parasite antigens" relates to one or more antibodies directed against a parasite antigen that are produced upon an infection of the subject. Preferably, the antibodies against parasite antigens used in the present invention can be a purified or semi-purified monoclonal antibody, a purified or semi-purified polyclonal antibody or an antiserum. Antiparasitic antibodies used in the present invention are selected from the group comprising Toxoplasma, Trypanosoma, *Plasmodium*. Particularly, antibody is directed against a specific antigen of Trypanosma Cruzi which is responsible for the Chagas disease. More particularly, antibody is directed against *Plasmodium*, preferably against *Plasmodium facliparum* which is responsible for malaria.

As used herein the term "anti-immunoglobulins" relates to antibodies directed against one or more immunoglobulins such as IgG, IgM, IgA, IgD, and IgE.

As used herein, the term "anti-red blood cells antibodies" or "antibodies of red blood cells antigens" relates to one or more antibodies directed against one or more red blood cells antigens. Preferably, the antibodies of red blood cells antigens used in the present invention can be a purified or semi-purified monoclonal antibody, a purified or semi-purified polyclonal antibody or an antiserum. Agglutinins or lectins can also be used.

A non-exhaustive list of antibodies and antigens used in the invention follows:

TABLE 1

Non-exhaustive list of antigens and antibodies of red blood cells

| Antigen | Antibody | Example of reference clones | revelation Element |
|---|---|---|---|
| A (ABO1) | Ac Anti-A | BIRMA-1, 2525B8, 9113D10, 16243G2, 16247(3)E6, A98 | Red blood cells of the sample |
| B (ABO2) | Ac Anti-B | LB-2 and/or ES-4,, 164B5G10, 9621A8, 7821D9, B84, B97, GAMA110 | Red blood cells of the sample |
| AB (ABO3) | Ac Anti-AB | ES-4 and/or ES-15 and/or BH517, 16247E10, 152D12, 16245F11D8 | Red blood cells of the sample |
| H (H1) | Ac Anti-H | 109 34 C11 | |
| D (RH1) | Ac Anti-D | RUM-1 and/or MS-201 and/or MAD-2 and/or TH-28 and/or MS-26, HM10, P3X212 23 B10,, P3X212 11 F1, HM16, P3X65, P3X290, P3X249, P3X241, P3X61 | Red blood cells of the sample |
| C (RH2) | Ac Anti-C | MS-273 or MS-24, P3X255 13 G8, DGC02 | Red blood cells of the sample |
| c (RH4) | Ac Anti-c | MS-33, RH4 951 | Red blood cells of the sample |
| E (RH3) | Ac Anti-E | MS-258, MS-80, P3X234, RH3 906 | Red blood cells of the sample |
| e (RH5) | Ac Anti-e | MS-16, MS-21, MS-63, MS-69, MS-62, HS128, P3GD C512 | Red blood cells of the sample |
| K (KEL1) | Ac Anti-K | MS-56, K 601 | Red blood cells of the sample |
| Fya (FY1) | Ac Anti-Fya | P3TIM, F655 | Red blood cells of the sample |
| Fyb (FY2) | Ac Anti-Fyb | SpA264LBg1 | Red blood cells of the sample |
| Jka (JK1) | Ac Anti-Jka | MS-15, P HT7 | Red blood cells of the sample |
| Jkb (JK2) | Ac Anti-Jkb | MS-8, P3 143 | Red blood cells of the sample |
| S (MNS3) | Ac Anti-S | MS-94, P3S13JS13 | Red blood cells of the sample |
| s (MNS4) | Ac Anti-s | P3BER L, P3 YAN | Red blood cells of the sample |
| Lea (LE1) | Ac Anti-Lea | LM112/161, 13649B9 | Red blood cells of the sample |
| Leb (LE2) | Ac Anti-Leb | LM129/181, GX336 | Red blood cells of the sample |
| M (MNS1) | Ac Anti-M | M110/140, 2514E6, M2A1 | Red blood cells of the sample |
| N (MNS2) | Ac Anti-N | 1422C7, 12E.A1 | Red blood cells of the sample |
| P1 | Ac Anti-P1 | P3MON23, P1650, OSK17 | Red blood cells of the sample |
| Kpa (KEL3) | Ac Anti-Kpa* | | Red blood cells of the sample |
| Lua (LU1) | Ac Anti-Lua* | | Red blood cells of the sample |
| Lub (LU2) | Ac Anti-Lub | OL67 | Red blood cells of the sample |
| k, cellano (KEL 2) | Ac Anti-k | P3A11 | Red blood cells of the sample |
| Kpb (KEL4) | Ac Anti-Kpb* | | Red blood cells of the sample |
| Cw (RH8) | Ac Anti-Cw | MS110 | Red blood cells of the sample |
| C3d | Ac Anti-C3d | 120 11 D10D10, 139 4B4 | Red blood cells of the sample |

*Polyclonal antibodies

The most of the above listed antibodies may be purchased from the applicant Diagast. According to one embodiment of the present invention, the antibodies fixed or adsorbed on the bead surface are anti-red blood cells antibodies selected from any one of antibodies in Table 1. For example, the anti-red blood cells antibodies may be selected from the group comprising antibodies Anti-A, Anti-B, Anti-AB, Anti-D, Anti-RH2, Anti-RH3, Anti-RH4, Anti-RH5 et Anti-Kell, anti-MNS (MNS1, 2, 3 and 4), Anti-JK (JK1, JK2), anti-FY (FY1, FY2), anti-LE (LE1, LE2), anti-LU (LU1, LU2) and anti-P1PK.

In the context of the present invention the term "antigen" relates to a predetermined molecule to which an antibody can selectively bind. The target antigen may be a polypeptide, a carbohydrate, a nucleic acid, a lipid, a hapten, a glycoprotein or a glycolipid or any other naturally occurring or synthetic compound. Preferably, the target antigen is a polypeptide, a glycoprotein or a glycolipid.

According to one preferred embodiment of the present invention, the antigens are selected from the group comprising red blood cells antigens (as listed in table 1), platelet antigens, viral antigens, bacterial antigens and parasite antigens, more preferably from the red blood cells antibodies or viral antigens. Preferably, the antigens used in the present invention can be a purified or semi-purified native antigen, a recombinant or a synthetic antigen.

As used herein, the term "viral antigen" relates to an antigen with multiple antigenicities that is strain-specific and closely associated with the virus particle. This antigen may be natural or recombinant protein. The viral antigens may be selected for example in the group comprising the antigens specific to Chikungunya, Cytomegalovirus, Dengue, Ebola, EBV, Encephalitis, Feline Leukemia Virus, Hantavirus, Hepatitis A, Hepatitis B (HBsAg), Hepatitis C (HCsAg), Hepatitis D, Hepatitis E, Herpes, HIV, HTLV, Influenza Lassa, Measles, Mumps, Norovirus, Papillomavirus, Parvovirus, Rubella, SARS, Varicella, West Nile virus and Zika. Particularly, the present invention relates to the identification and/or the detection of antigens HBsAg and HCsAg since they are mandatory for blood transfusion safety, more particularly to HBsAg.

As used herein, the term "bacterial antigen" relates to a molecule that is found on the surfaces of bacterial organisms. Bacterial antigens may be selected from any one of bacterial strains but are preferably selected from *Borrelia, Chlamydia, Helicobacter Pylori, Mycoplasma, S. Typhi, Yersinia, Proteus, Pseudomonas, Escherichia, Klebsiella, Acinetobacter, Serratia, Clostridium, Propionibacterium, Staphylococcus, Bacillus*, and *Enterococcus*. Particularly, a specific antigen of bacterium *Treponema pallidum* which is responsible for syphilis may be detected and/or identified or may be fixed and/or adsorbed on the bead surface.

As used herein, the term "parasite antigen" relates to a molecule that is found on the surface of parasite cell. The parasite may be as defined above. Preferably, parasite antigens are selected from the group comprising antigens specific to Toxoplasma, Trypanosoma, *Plasmodium*, more preferable antigens specific to *Plasmodium*, particularly to *Plasmodium falciparum* causing malaria.

Non-exhaustive list of antigens and antibodies directed against virus, bacteria and parasites antigens is given in Table 2 below:

TABLE 2

Non-exhaustive list of antigens and antibodies directed against virus, bacteria and parasites antigens

| Antigens | Antibodies | Example of reference and providers | revelation Element |
|---|---|---|---|
| HBsAg protein Subtype ad from hepatitis B virus | Anti-HBsAg | 10-H05H (mouse IgG2B) and 10-H05G (mouse (IgG1b) from Fitzgerald industries | 1 μm colored beads |
| p15, p17, p47 *Treponema Pallidum* | Anti-p15, anti-p17 and anti-47 | 20TR-89 (Rabbit IgG) IgG2B) from Fitzgerald industries | 1 μm colored beads |
| Merozoite surface protein-1 (MSP1) from *Plasmodium falciparum* | Anti-MSP1 | Positive control from Anti-malaria Elisa Kit from Abcam | HRP-coupled anti-human IgG/IgM; colloidal gold nanoparticles or 1 μm colored beads |

As used herein, the term "platelet antigen" relates to an antigen of platelet related to all immunogenic molecules present at the surface of platelets, where needed able to cause the production of antibodies directed against these molecules and/or allow their recognition. The platelet antigens may be selected for example in the group comprising the biallelic antigen HPA-1, -2, -3, -4, -5 and -15.

As used herein, the term "red blood cells antigens" also known as an antigen of blood group relates to all immunogenic molecules present at the surface of red blood cells, where needed able to cause the production of antibodies directed against these molecules and/or allow their recognition. The red blood cells antigens include a mixed field population antigens. A non-exhaustive list of red blood cells antigens is shown in Table 1.

As used herein, the term "mixed-field population" relates to two populations of red blood cells with different antigens that may be observed after transfusion with compatible red blood cells between the donor and the recipient (O red blood cells transfused in A or B patients) or after bone marrow transplantation. The in vitro device of the invention allows detection of a sample with a mixed-field population.

As used herein, the term "in vivo-sensitized red blood cells" relates to red blood cells with immunoglobulin (IgG) or complement (C3d) bound in vivo to their membrane surface. In vivo-sensitized red blood cells may appear in different clinical hemolytic conditions including hemolytic transfusion reactions, hemolytic disease of the fetus and newborn (HDFN), autoimmune hemolytic anemia (AIHA), and drug-induced antibodies in the patient.

According to another embodiment of the present invention said antibody and/or antigen is directly or indirectly fixed or adsorbed on the bead surface.

There are currently several means of attaching biological ligands to the beads used as solid phase supports in immunological tests and assays, including adsorption to plain polymeric beads, covalent attachment to surface functionalized microspheres. The mechanism for adsorption is based primarily on hydrophobic (Vander Waals, London Type) attractions between the hydrophobic portions of the adsorbed ligands and the polymeric surface of the bead. This is the means of mainly consists of covalent coupling for the immobilization of biomolecules when a very active and stable bead reagent is required whereas indirect fixation is mediated by an anti-immunoglobulins, such as anti-human globulin (AHG), fixed covalently or adsorbed on the beads that capture a second antibody directed against the antigen of interest.

When the antibody and/or the antigen is directly fixed or adsorbed on the bead surface, that is performed by contacting the beads with the antibodies and/or the antigens. For example, the solution containing the antibodies and/or the antigens may be a non-denaturing buffer comprising a pH solution stabilised between pH 4 and pH 10, preferably between pH 6.5 and pH 7.8, even more preferably between pH 7 and pH 7.5. The antibodies can be either adsorbed or be linked covalently.

The antibody solutions are selected from culture supernatants, or concentrates of supernatants, purified antibodies, semi-purified or enriched antibodies. The antigen solutions are selected from purified or semi-purified native antigen, a recombinant or a synthetic antigen. The antibodies and/or the antigens can be added to adjuvants intended to maintain their microbiological stability such as sodium azide, antibiotics and its conformational stability such as sugars (sucrose, dextrose, trehalose), as well as any other agent known to those skilled in the art to perform these functions.

According to one embodiment, the bead surface comprises at least one chemical group selected from aldehyde groups, chloromethyl group, NHS groups and carboxyl groups.

Particularly, when the bead surface comprises an aldehyde groups, this group reacts with the amino group of the antibody which allow to directly fix the antibody directed to the antigen to be determined and/or to be identified or the antibodies used for indirect fixation (described below) to the surface of the bead. In case of the fixation of an antigen, this group reacts with the amino group of the antigen which allow to directly fix the antigen recognized by the antibodies to be determined and/or to be identified.

In another particular embodiment, the bead surface comprise NHS groups or also called N-hydroxysuccinimide (NHS) functional groups, preferably it comprises NHS-ester functional groups.

According to another embodiment of the present invention, the antibody directed to the antigen to be determined and/or to be identified or to the known antigen may be indirectly fixed to the bead surface via another antibody, an anti-immunoglobulin for example. Such anti-immunoglobulin is preferable directed against immunoglobulins, more preferably an IgM or an IgG. In this case, if the bead surface contains an aldehyde group, the amino group of anti-immunoglobulin reacts with the aldehyde group, fixing in this manner the anti-immunoglobulins to the bead surface. The antibody directed to the antigen to be determined and/or to be identified is then fixed to anti-immunoglobulin via protein/protein interaction.

According to still another embodiment, the antibody directed to the antigen to be determined and/or to be identified or to the known antigen may be indirectly fixed to the bead surface via a ligand selected from proteins with affinity for antibodies such as protein A, protein G and/or protein L.

The beads deposed on the porous membrane of the in vitro device of the invention may be performed from different types of materials such as glass, polymer, particularly latex. Preferably the beads are selected from the group of glass beads, COOH functionalized polystyrene beads, protein A/G and/or L functionalized agarose beads, NHS functionalized agarose beads, epoxy functionalized beads, chloromethyl functionalized latex beads or aldehyde functionalized beads.

More preferably, the beads are latex beads, particularly aldehyde functionalized latex beads.

According to one embodiment, the beads are used at concentration comprised between 1% and 10%, preferably between 1% and 5%, more preferably between 2% and 6% or 1% to 3%, even more preferably 3% of the solution deposited on the hydrophilized reaction area of the porous membrane, the deposited volume of said solution is comprised between 1 and 100 µl, preferably between 1 and 50 µl, more preferably between 5 and 50 µl and even more preferably between 1 and 10 µl or 5 and 10 µl.

The size of beads is selected as function of the size of pore of the hydrophobic porous membrane. The beads' size have to be superior than the size of the pores of the porous membrane in order to avoid the absorption of beads in the porous membrane. However, the beads' size has not to be very important in order to avoid the agglutination phenomena. The skilled artisan would be able to select the size of the bead depending on the size of pores of the porous membrane.

In one preferred embodiment of the present invention, the size of beads is comprised between 1 µm and 130 µm, preferably between 5 µm and 20 µm and it is more preferably 9 µm.

According to one embodiment of the in vitro device according to the invention, the porous membrane has a thickness comprised between 0.4 mm and 2 mm, preferably between 0.6 mm and 1.5 mm.

The hydrophobic porous membrane can comprise any material which is not altered by aqueous solvents. This material can especially be selected from natural polymers modified chemically or not, such as for example nitrocellulose polymer, cellulose or from synthetic polymers such as for example polyethylene, high-density polyethylene (HDPE) or fluorinated polymers such as polyvinylidene fluoride (PVDF), preferably polyethylene. These polymers can be functionalised or not with reagent groups capable of creating links with the capturing agents used later.

The hydrophobic porous membrane comprises at least one hydrophilic reaction area on which are deposited the beads. The reaction area has a surface less than the surface of the hydrophobic porous membrane, that is, the membrane cannot be fully hydrophilized.

The hydrophilic reaction area(s) of the porous membrane have preferably been made hydrophilic by addition of surfactant locally, without modification of the chemical functions of the porous substrate by prior chemical or physical treatment of the hydrophobic porous membrane.

In the context of the present invention, the term "surfactant" means any hydrophilizing agent, that is, any substance capable of making hydrophilic the hydrophobic membrane at manner sufficient to pass through, by capillarity, the sample containing tested analytes.

The surfactant used can be selected from natural surfactants, natural surfactants modified chemically or obtained by chemical synthesis. Preferably, this is a non-ionic surfactant, for example Triton X-100, Tween 20 or saponin, polyoxyethylene or nonyl-β-D glucoside.

The surfactant can be diluted in an aqueous solution or an organic solvent such as ethanol, at a concentration between 0.01 and 5% (weight/volume). Preferably, the surfactant used to make the membrane locally hydrophilic is used at concentration between 0.1% and 3%, more preferably between 0.5 and 2% and even more preferably between 0.5 and 1% (weight/volume).

In order to hydrophilize hydrophobic porous membrane, 0.1 to 5 µl, preferably 0.3 to 3 µl, more preferably 0.5 to 2 µl of the solution containing the surfactant are deposited on the membrane.

Thus, according to one embodiment, the hydrophilic reaction area of the hydrophobic porous membrane is rendered hydrophilic by a surfactant, preferably used at concentration comprised between 0.01 and 5% w/v, more preferably between 0.1% and 3% w/v, even more preferably between 0.5% and 2% w/v of a solution and wherein 0.1 to 5 µl, preferably 0.3 to 3 µl and more preferably 0.5 to 2 µl of said solution containing the surfactant is deposed on the hydrophobic porous membrane.

The concentration of the surfactant used, correlated to the other characteristics of the membrane (porosity and thickness in particular) controls the motion speed of fluids which pass through the membrane. It is generally admitted that a maximal dose of 0.1% for the Triton X-100 and 0.05% for the Tween does not need to be exceeded to make hydrophilic a membrane intended to receive a capturing element. But because of the particular characteristics of the membrane according to the invention, detergents capable of making this membrane hydrophilic locally can be used up to 5%, preferably up to 3% especially for Triton X-100 or Tween-20, without disrupting the reactivity of the area, which makes hydrophilization of the membrane easier.

A same hydrophobic membrane can comprise several hydrophilic reaction areas, on condition that these areas do not intersect.

The reaction areas can be in all geometric forms, but preferably in the form of circles or spots of diameter between 0.3 mm and 20 mm.

The reaction area can be hydrophilic over the entire thickness of the porous membrane and/or at the surface.

The reaction area can have a single degree of hydrophilization, i.e. the reaction area has the same degree of hydrophilization.

According to one embodiment, the reaction area can comprise several areas having different degrees of hydrophilization. For example, the reaction area can comprise two hydrophilic areas with a greater degree of hydrophilization at the centre of the reaction area than at the periphery. These hydrophilic areas are preferably only at the surface of the membrane.

The reaction area can also comprise two hydrophilic areas with a different degree of hydrophilization, one at the surface, and the other in the thickness.

In the case where a reaction area comprises two hydrophilic areas, the reaction area has been made hydrophilic with two different surfactants without modification of chemical functions of the porous substrate by prior chemical or physical treatment of the porous membrane.

Advantageously, the configuration of the reaction area with two regions having different hydrophilization, in particular at the surface, is useful when detecting a mixed-field population from a sample of blood or blood components.

This configuration is also particularly adapted to detection and/or identification of particular antibodies and/or antigens in the sample to be tested.

The in vitro device of the invention, according to one embodiment, can comprise an absorbent layer (or also called absorbent membrane) arranged underneath the porous membrane. This layer absorbs liquids deposited at the level of the reaction areas, which are not retained by the porous membrane, in particular when the reaction area is hydrophilic over the entire thickness of the membrane.

The absorbent layer can comprise material enabling passive absorption by capillarity such as absorbent paper, cellulose, etc., or made of absorbent polymers. By way of example, the following products can be cited to be used as absorbent layer:

MerckMillipore® C048, C068, C083, C248 (Merck)
Whatman® CF3, CF4, CF10, Grade 470, CFS, CF6, CF7, Grade 900, Grade 300
Ahlstrom® Grades 601, 642, 631, 238, 237, 222, 243, 320 (Munktell)
Pall Grades 111, 113, 133, 165, 197, 8975, 8964, 8301 (Pall Corporation), Membrane for the Direct Collection, Storage, and Efficient Rapid Release of Biological Samples for Clinical Diagnostics Accuwik® Ultra
Cleanis Gelmax® superabsorbent pad.
Mc Arlaid T-499, SCP-300-TCF, T-089, T-183-5 and SCP-200-TCF The composition of the absorbent membrane and its dimensions must be selected so they can absorb all the solutions used during the test ($V_{total}$ in µl). Each membrane being characterized by an absorption capacity (C in µl/cm$^2$), the membrane and its dimensions (D in cm$^2$) are selected to satisfy the following equation: $D > V_{total}/C$.

According to one embodiment, the in vitro device of the invention also comprises at least another layer arranged between the porous hydrophobic membrane and the adsorbing layer, said layer is made from draining material. The draining material is such as for example cotton wool, NA7150PES, NT9610HY, NT9750HY NV170F, NV250F, NV340F, (Subrenat) or Packtex HY050B.

The porous membrane and optionally the absorbent and draining layers, are arranged in a support of the device.

The support of the in vitro device according to the invention is preferably a rigid support. It can be for example a shell.

The support preferably comprises rigid material not letting liquid escape. This can be in particular plastic materials such as polypropylene, polyethylene, polystyrene, acrylonitrile butadiene styrene, polyethylene terephthalate, polycarbonate, polyamide, polyvinyl chloride, methyl poly-methacrylate.

The support of the in vitro device of the invention preferably comprise two parts, a lower part on which is disposed the hydrophobic porous membrane, the draining layer and the absorbent layer and upper part which cover the lower part.

Preferably, on the surface of the lower part of the support is arranged absorbent layer on which is disposed the hydrophobic porous membrane. More preferably, between the absorbent layer and the porous membrane is arranged an draining layer. Even more preferably, on the surface of the lower part of the support is arranged a layer of foam, on which is deposited the absorbent layer, then the draining layer, on which is deposited the hydrophobic porous membrane comprising at least on hydrophilic reaction area which surface is less than the surface of the membrane and on the reaction area are deposited the bead with the antibodies fixed and/or adsorbed on their surface (FIGS. 1a and b).

The upper part of the support covers the lower part such as the hydrophobic porous membrane and any one of or all of the others layers when they are present in the support, may be enveloped in the support.

The upper part of the support preferably comprises at least one or more openings. This opening(s) corresponds to the collection area of the sample deposited on the hydrophilic reaction area. The hydrophilic area can be of a size identical to that of the base of the opening, smaller or larger provided two hydrophilic areas are always separated by a hydrophobic area on the membrane.

The collection area must be of a size such that it can contain at least the maximum volume of sample or the reaction mix to be tested deposited on the reaction membrane.

According to one embodiment, the different parts of the in vitro device of the invention may be assembled by the user if they are supplied as a kit. The device may be supplied in one piece.

As indicated above, the in vitro device of the invention can also detect and/or identify an antibody.

According to one embodiment, the detection of antibody is performed via the binding of specific known antigen fixed and/or adsorbed on the bead surface. The antibody to be identified and/or to be determined in the sample of biological fluid can bind specifically the known antigen. The detection of this binding allows detecting the antibody specifically directed against said antigen.

According to another embodiment of the invention, the detection of antibodies may be performed by fixing or adsorbing an anti-immunoglobulin (antibody) on the bead surface which is anti-immunoglobulin able to bind another antibody (to be detected and/or identified) present in the sample to be tested. The second antibody will be then detected and/or identified by using a revelation agent, for example a labelled antigen specifically binding this antibody.

According to another embodiment of the invention, the detection of antibodies may be performed by fixing or adsorbing a protein with affinity for antibodies on the bead surface which is able to bind an antibody (to be detected and/or identified) present in the sample to be tested. The antibody will be then detected and/or identified by using a revelation agent, for example a labelled antigen specifically binding this antibody.

In one embodiment, when the anti-red blood cell antibodies are determined and/or identified, the beads fix or adsorb an anti-immunoglobulin (anti-IgG and/or anti-IgM) which will capture the circulating anti-red blood cells antibodies in the blood sample, especially serum or plasma. The revelation and the identification of these antibodies may be carried out using red blood cells carrying the corresponding antigen.

In one embodiment, when the anti-red blood cell antibodies are determined and/or identified, the beads fix or adsorb an anti-immunoglobulin (anti-IgG and/or anti-IgM) which will capture the anti-red blood cells antibodies present at the surface of in vivo sensitized red blood cells. The revelation and the identification of these antibodies are carried out by the in vivo sensitized red blood cells themselves.

In one embodiment, the beads fix or adsorb an anti-C3d antibody which will capture the in vivo complement-sensitized red blood cells that result from activation of the complement by the in vivo fixation of IgM-type anti-red blood cells antibody. The revelation and the identification of these antibodies are carried out by the in vivo sensitized red blood cells themselves.

The same principle can be applied to antibodies directed against viral, bacterial or parasite antigens which circulate in the blood of the tested subject suspected to be infected, using for example a different system of revelation such as for example a second set of colored beads coupled with the corresponding antigens or an antibody conjugated with an enzyme (for example, the horseradish peroxidase) or with colloidal gold nanoparticles.

The in vitro device of the present invention is intended to determinate and/or identify an antigen and/or an antibody from a sample of biological fluids.

In the context of the present invention, the term "sample of biological fluid" relates to any sample obtaining from bio-organic fluids produced by a life organism. The biological fluids are selected from the group comprising extracellular fluids, intravascular fluids, interstitial fluids, lymphatic fluids and transcellular fluids. Particularly, the sample of biological fluid is selected from the group comprising blood and blood components, urine, saliva, etc.

In more preferred embodiment the sample of biological fluid is a sample of blood or a sample of blood components. "Sample of blood" or "sample of blood components" means the total blood or one of its components selected especially from the red cells fraction, white cells fraction, platelets, plasma or serum.

Particularly, when the in vitro device of the present invention is used for detecting and/or identifying red blood cells antigens and/or antibodies directed against these antigens, the sample is a blood sample or sample of blood components.

Particularly, when the in vitro device of the present invention is used for detecting and/or identifying viral, bacterial or parasite antigens and/or antibodies directed against these antigens, the sample is a blood sample or sample of blood components.

The sample as described above may be obtained from any organism, particularly from mammal and more particularly from human being.

Preferred Embodiments

Various preferred specific features corresponding to various generic elements of the in vitro device according to the invention have been described above in the section specifically relating to this element. In the context of the invention, each list of appropriate features for a particular element and each specific feature disclosed for a particular element may be combined with any generic other element, list of appropriate features for said other element or any specific feature disclosed for said other element.

In particular, preferred embodiments of an element of the in vitro device according to the invention may be combined with any generic other element or with preferred embodiments of said other element.

Preferred embodiments correspond to those in which at least one element is limited to a preferred embodiment, as listed in Table 3 below:

TABLE 3

Preferred embodiment of various elements of the in vitro device according to the present invention

| Element | Preferred embodiment(s) |
| --- | --- |
| Layers arranged on the support | Foam, Absorbent layer, Draining material and Porous hydrophobic membrane |
| Hydrophobic porous membrane: thickness | between 0.6 and 1.5 mm |
| concentration of the surfactant and volume of the solution use for the hydrophilization of the membrane | between 0.5 and 2% (w/v); between 0.5 and 2 µl |
| Antibodie or antigen fixed or adsorbed on the bead surface is selected from the following list: | anti-red blood cells antibodies<br>anti-immunoglobulins<br>red blood cells antigens<br>platelet antigens<br>antiplatelet antibodies<br>viral antigens<br>bacterial antigens<br>parasite antigens<br>antiviral antibodies<br>antibacterial antibodies<br>antiparasite antibodies |
| Ligands for indirect binding of the antibodies to the bead | Anti-immunoglobulins: IgG or IgM; Proteins: A, G and/or L |
| Beads:<br>structure of the bead surface | aldehyde group |
| mean size | between 8 and 10 µm |
| concentration of beads and volume of the bead solutions deposed on the reaction area | between 2 and 6% or 1 and 3%; between 1 and 10 µl or 5 and 10 µl |

Use of the In Vitro Device of the Invention

The in vitro device of the invention may be used for detecting and/or for identifying an antigen and/or an antibody from a sample of biological fluid.

As indicating above this device is suitable for detecting and/or identifying any antigen and/or any antibody depending on the antibody and/or the antigen fixed or adsorbed on the bead surface.

The inventors have conducted investigations in order to demonstrate that the in vitro device of the present invention is suitable for use with antibodies fixed on the beads surface having structural differences such as the antibodies directed against blood cells antigens and antibody directed against at least on antigen specific to virus, bacteria or parasite. For example, the tested antibody is one directed against an antigen of HCV (HCsAg) or HBV (HBsAg), causing Hepatitis C and B respectively, said antibody may be fixed or adsorbed on the bead surface in order to detect and/or identify the cited antigens respectively. Preferably, said antibody is one directed against an antigen HBV (HBsAg.)

Particularly, the inventors demonstrated that the in vitro device of the present invention is useful for detecting and/or identifying antigens and/or antibodies of red blood cells, viruses, bacteria and parasites from biological fluid, particularly from sample of blood or sample of blood components.

According to another aspect, the present invention thus relates to a use of the in vitro device according to the invention for determining and/or identifying:
- at least one antigens selected from the group comprising red blood cells antigens including a mixed-field population, platelet antigens, viral antigens, bacterial antigens and parasite antigens;
- at least one antibody selected from the group comprising anti-red blood cells antibodies, antiplatelet antigens, antiviral antibodies, antibacterial antibodies and antiparasitic antibodies from a sample of biological fluids, preferably from a sample of blood or a sample of blood components from a sample of biological fluids, preferably from a sample of blood or a sample of blood components.

As indicated above, different types of antigens or antibodies may be detected and/or identified by the in vitro device of the invention depending on the type of antibodies or antigens fixed or adsorbed on the bead surface.

Particularly, the in vitro device of the present invention is used for detecting and/or identifying antigens of the group comprising red blood cells antigens, platelet antigens, viral antigens, bacterial antigens and parasite antigens. More particularly, the device is used for detecting and/or identifying red blood cells antigens.

The in vitro device of the present invention can be used especially for determining and/or identifying (or also phenotyping) the red blood cells, that is, the determination of antigens at their surface. The phenotyping of red blood cells usually means, determining and/or identifying the blood groups. In the context of the present invention, the term "blood group" relates for example to groups selected from ABO, D, Rh, Kell, MNS, JK (Kidd), FY (Duffy), LE (Lewis), LU (Lutheran), P1PK systems.

The in vitro device of the present invention is also used for detecting and/or for identifying antibodies selected from the group comprising anti-red blood cells antibodies or also called anti-blood cells antibodies which comprise autoantibodies, alloantibodies, heteroantibodies and cold antiglobulin. Particularly, these antibodies are detected and/or identified from sample of blood or sample of blood components.

The in vitro device of the present invention can be used especially for:
Simonin-Michon test which identifies the presence of anti-A (anti-ABO1) or anti-B (anti-ABO2) antibodies;
Search for or identification of antibodies directed against cellular antigens in particular red blood cells in terms of the search for alloantibodies, autoantibodies, heteroantibodies or even cold agglutinins by indirect antiglobulin test;

Search for compatibility between donor's red blood cells and recipient's blood by performing a crossmatching reaction;

Search for antibodies fixed in vivo on red blood cells by direct antiglobulin test.

As used herein, the term "alloantibody" relates to one or more antibodies produced by a subject that reacts with one or more antigen from a genetically different individual of the same species. These alloantibodies are produced by immunization following a blood transfusion, during pregnancy, after transplantation or graft.

As used herein, the term "autoantibody" relates to one or more antibodies produced from a subject directed against one or more antigens of the same subject. The detection of autoantibodies is preferably performed after blood transfusion or in case of haemolytic anaemia (auto-immunes, drug induced or after blood transfusion).

As used herein, the term "heteroantibody" relates to one or more antibodies produced from a subject directed against one or more antigens from another species.

As used herein, the term "cold agglutinin" relates to antibodies which cause red blood cells agglutination at low temperatures.

As used herein, the term "crossmatching reaction" relates to a test which is performed before a blood transfusion to determine if the donor's red blood cells are compatible with the blood or the plasma of an intended recipient.

The antiviral, antibacterial and antiparasitic antibodies detected and/or identifying by the in vitro device are immune antibodies produced against viral, bacterial or parasite antigens upon infection of a subject.

The in vitro device of the present invention can also be used for detecting the presence of an pathogen agent by determining the presence of one or more viral, bacterial or parasite antigens Methods of the Invention The in vitro device of the invention is particularly suitable for using in in vitro methods for detecting and/or identifying antigens selected from the group comprising red blood cell antigens including a mixed-field population, in vivo sensitized red blood cells (also called C3d-positive cells), platelet antigens, viral antigens, bacterial antigens, parasite antigens, or for detecting and/or identifying anti-red blood cells antibodies, including in vivo sensitized red blood cells (IgG-positive cells), and/or antiplatelet antibodies and/or antibodies directed against viral, bacterial and parasite antigens that are produced against viral, bacterial or parasite antigens upon infection of a subject present in the blood.

According to another aspect, the present invention thus relates to an in vitro method for detecting and/or identifying red blood cell antigens including a mixed-field population, and/or in vivo sensitized red blood cells (C3d-positive cells) and/or platelets antigens from a sample of blood or a sample of blood components comprising the following steps adding a solution containing said sample on the reaction area of the in vitro device according to the invention, and reading before rinsing for sample load control;
depositing a rinse solution on the reaction area, and
determining the presence of said antigens or blood cells by determining the presence of an antigen/antibody interaction if in the reaction area appears a red or pink spot or determining the absence of said antigens or blood cells by determining the absence of an antigen/antibody interaction if in the reaction area appears a colourless spot.

According to one embodiment, prior to deposit of the sample to be tested on the reaction area comprising the beads, it is possible to proceed with hydration of the reaction area, which was already hydrophilized, by means of a buffer solution. This buffer can comprise a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain surfactant in low concentration (Tween 20 from 0.01 to 0.05% m/v), saturation agents (BSA) and/or agents capable of potentializing antigen-antibody reactions. The buffer can optionally have protease activity for example obtained by the addition of enzymes such as papain or bromelain. This buffer can optionally contain polycationic agents such as polybrene or polylysin, for potentializing the reaction and keeping the red blood cells in longer contact with the capturing elements.

The in vitro method above thus optionally comprises a step of hydration of the porous membrane before adding the tested sample.

According to another embodiment, the in vitro method above also comprises another optional step of diluting the red blood cells to be phenotyped in a buffer solution, specifically a buffer solution known to be favourable to immuno-haematological reactions optionally containing additives, such as for example a buffer comprising a solution of stabilised pH between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (especially Tween 20 from 0.01 to 0.05% m/v), saturation agents (for example BSA) and/or agents capable of potentializing antigen-antibody reactions. This buffer can optionally have protease activity for example obtained by the addition of enzymes such as papain or bromelain. This buffer can optionally contain polycationic agents such as polybrene or polylysin, for potentializing the reaction and keeping the globules in longer contact with the capturing element.

According to still another embodiment, the method of the invention described above optionally comprises an additional step of incubating the tested sample before depositing it on the reaction area, preferably at a temperature between 15 and 40° C. in particular between 18° C. and 37° C., for a period from 2 sec to 30 min and in particular from 1 min to 20 min.

Similarly, to read the results it is necessary to implement a step of buffer rinsing. The washing buffer preferably comprises PBS, TBS or saline solution of pH between 2 and 10, preferably between 5 and 9. The osmolarity of the buffer must be controlled to avoid haemolysis of red blood cells. The buffer must be selected so as not to detach the revelation agents or the coloured analytes fixed directly or indirectly to the capturing agents (antibodies fixed and/or adsorbed on the bead surface). Surprisingly, for use of the in vitro device according to the invention it is preferable to use lightly hyperosmotic washing solutions (that is, between 300 mOsm and 800 mOsm) obtained by the presence of saline agents such as NaCl or non-ionic osmolites such as for example glycine or taurine. This buffer can optionally be coloured with colours contrasting with the colour of the revelation agent. For example if the revelation agents are red blood cells, the washing buffer solution can be coloured blue or green. It is also possible to add a low dose of surfactant to the washing solution to eliminate background noise. These surfactants are preferably non-ionic surfactants, and in particular esters of sugar, especially polyoxyethylenic esters of sorbitan (Tween).

During the use of the in vitro device, liquids can be deposited especially by means of a pipette system or by means of a capillarity replication system.

In said in vitro method, the hydrophilization of reaction areas of the porous membrane of the in vitro device according to the invention can be thickness hydrophilization, i.e. hydrophilization performed through the entire thickness of the porous membrane.

Hydrophilization can be performed by means of an aqueous solution of Triton X100 of concentration between 0.01% m/v and 5% m/v, preferably 0.1% m/v and 3% w/v, preferably between 0.5% m/v and 2% m/v in volume between 0.1 µl and 5 µl, preferably between 0.3 µl and 3 µl and more preferably between 0.5 µl and 2 µl.

In some applications, when Triton is used, the hydrophilization of the porous membrane may be partial, that is to say that it is not done on the entire thickness of the membrane.

If the red blood cells present in the sample carry the antigen (antigens of the red blood cells or antibodies fixed on in-vivo-sensitized red blood cells) recognised by the specific antibody fixed or adsorbed on the bead surface, the red blood cells remain immobilised on the bead surface disposed on the reaction area in spite of the rinsing and the reaction area remains red or pink. If the red blood cells present in the sample do not carry the antigen recognised by the antibody fixed or adsorbed on the bead surface, the red blood cells are flushed by the rinsing solution and the reaction area remains colourless.

Reading the results can be visual or automatic.

The detection and/or the identification of in vivo sensitized red blood cells allows detecting autoantibodies or alloantibodies adsorbed at the surface of the red blood cells. Particularly, this detection is based on the use of beads coupled with anti-immunoglobulins (anti-IgG) or an anti-C3d antibody (for IgM) that will capture the red blood cells to be tested via IgG or C3d (whose formation is induced by IgM) fixed on their membrane.

Advantageously, the device according to the invention needs neither centrifuging, nor agitation, nor vacuuming, nor ad hoc device. It can also be used manually totally autonomously, and easily be automated on robots.

Moreover, the inventors have also demonstrated that the in vitro device of the present invention may be used in an in vitro method for detecting and/or for identifying anti-red blood cells antibodies (alloantibodies, autoantibodies and cold agglutinin) from a sample of biological fluid, particularly from a sample of blood or blood components.

Another aspect of the present invention thus relates to an in vitro method for detecting and/or identifying anti-red blood cells antibodies from a sample of blood or a sample of blood components, comprising the following steps:
  incubating the sample to be tested with a buffer and red blood cell tests of known phenotype,
  depositing the mixture on the reaction area of the in vitro device according to the invention,
  depositing a rinse solution on the reaction area, and
  determining the presence of anti-red blood cell antibodies by determining the presence of antibody/antigen reaction if in the reaction area appears a red or pink spot or determining the absence of said antibodies by determining the absence of antibody/antigen reaction if in the reaction area appears a colourless spot.

The incubating step may be performed in the presence of an agent capable of aggregating the red blood cells at a temperature between 4 and 40° C., for a period of between 3 and 60 min, preferably between 5 and 30 min. The skilled artisan would be able to determine the temperature depending on antibody to be detected and/or identified The buffer used in the incubating step is a buffer of low ionic force, such as a LISS buffer (for example containing fewer than 50 mM NaCl).

According to one embodiment of this method, adding an agent capable of aggregating the red blood cells, for example a solution of hexadimethrine bromide preferably a hexadimethrine bromide at concentration in the solution between 0.01 and 2% (m/v), even more preferably between 0.05 and 0.5% may be added to the mixture obtained in the step of incubation. Hexadimethrine bromide promote the red blood cells aggregation.

According to another embodiment of the method for detecting and/or identifying ant-red blood cells antibodies, human antiglobulin or anti-complement reagent may be deposited on the reaction area after the depositing of the agent capable of aggregating the red blood cells.

The rinse solution used for rinsing the reaction area may be such as for example a hypertonic saline solution of stabilised pH between pH 6 and pH 8.5, preferably between pH 6.5 and pH 7.8, preferably between pH 7 and pH 7.5 and osmolarity between 300 mOsm and 800 mOsm. This solution can optionally contain detergents in low concentration (for example Tween 20 0.01 to 0.05% m/v) and a dye of a colour contrasting with red (blue or green).

The sample to be deposited can be plasma, serum or total blood or blood components diluted or not in a buffer comprising a stabilised pH solution between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (for example Tween 20 0.01 to 0.05% m/v), saturation agents (especially BSA) and/or agents capable of potentializing antigen-antibody reactions. This buffer preferably has salinity less than 50 mM in NaCl.

If the plasma tested contains antibodies directed against the antigen present in the revelation agent (red blood cell tests), a red (or pink) spot appears in the reaction area. A colourless centre means the absence or undetectable dose of antibodies directed against the antigen present in the revelation agent (red blood cell tests).

Reading the results can be visual or automatic.

Another aspect of the present invention further relates to an in vitro method for detecting and or identifying antiplatelet antibodies from a sample of blood or a sample of blood components, comprising the following steps:
  incubating the sample to be tested with a buffer and platelet tests of known antigenicity or incubating the recipient's plasma or serum with the donor's platelets,
  depositing the mixture on the reaction area of the in vitro device according to the invention,
  depositing a rinse solution on the reaction area, and
  determining the presence of antiplatelet antibodies by determining the presence of an antibody/antigen interaction if in the reaction area appears a red or pink spot or determining the absence of said antibodies by determining the absence of antigen/antibody interaction if in the reaction area appears a colourless spot.

The in vitro device of the invention may be also used in an in vitro method for detecting and/or identifying different type of antigens selected from the group comprising viral antigens, bacterial antigens and parasite antigens.

Still another aspect of the present invention thus relates to an in vitro method for detecting and/or identifying antigens selected from the group comprising viral antigens, bacterial antigens and parasite antigens from a sample of biological fluid, preferably from a blood sample or a sample of blood components comprising the following steps:

- optionally incubating the sample to be tested with a buffer,
- adding a solution containing said sample or mixture of the sample with the buffer on the reaction area of the in vitro device according to the invention,
- optionally reading before rinsing for sample load control;
- optionally depositing a rinse solution on the reaction area, and
- determining the presence of said antigen by determining the presence of an antigen/antibody interaction, preferably if in the reaction area appears colored spot or determining the absence of said antigens by determining the absence of an antigen/antibody reaction, preferably if in the reaction area appears a colourless spot.

The incubating step may be performed in the presence of an agent capable of increasing reaction at a temperature between 4 and 40° C., for a period of between 3 and 60 min, preferably between 5 and 30 min. The skilled artisan would be able to determine the appropriate temperature depending on antibody or antigens to be detected and/or identified.

The buffer used in the incubating step is a buffer with molecule for increasing reaction.

The sample to be deposited can be biological fluid example: plasma, serum or total blood or blood components diluted or not in a buffer comprising a stabilised pH solution between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (for example Tween 20 0.01 to 0.05% m/v), saturation agents (especially BSA) and/or agents capable of potentializing antigen-antibody reactions. This buffer preferably has salinity less than 50 mM in NaCl.

The rinse solution used for rinsing the reaction area may be such as for example a hypertonic saline solution of stabilised pH between pH 6 and pH 8.5, preferably between pH 6.5 and pH 7.8, preferably between pH 7 and pH 7.5 and osmolarity between 300 mOsm and 800 mOsm. This solution can optionally contain detergents in low concentration (for example Tween 20 0.01 to 0.05% m/v).

The revelation of the antigen/antibody interaction may be performed preferably by the use of colored beads or HRP (horseradish peroxidase) coupled to antibodies or other molecule which would interact with the corresponding pathogen antigens.

The skilled artisan would be able to determine other means of labeling allowing to detect and/or to identify said antigens.

If the plasma tested contains antigens directed against the antibody present in the revelation agent, a colourless spot appears in the reaction area. A colourless centre means the absence or undetectable dose of antigens directed against the antibody present in the revelation agent.

Reading the results can be visual or automatic.

As indicated above, the antibodies directed against antigens selected from the group of viral, bacterial or parasitic antigens may be also detected and/or identified using the in vitro device of the present invention. In fact, in the most of case when the presence or the absence of a pathogen (virus, bacteria or parasite) is determined during a blood transfusion for example, it is proceeded by the determination and/or the identification of antibodies produced by the infected subject directed against said antigens. These antibodies are also mentioned in the present application as immune antibodies produced against viral, bacterial or parasite antigens upon infection of a subject. They may circulate in the blood of the infected subject.

Thus, according to still another aspect, the in vitro device of the invention may be also used in an in vitro method for detecting and/or identifying different antibodies directed against viral antigens, bacterial antigens and parasite antigens that are produced upon infection of a subject.

Still another aspect of the present invention thus relates to an in vitro method for detecting and/or identifying antibodies selected from the group comprising antibodies directed against viral antigens, bacterial antigens and parasite antigens, preferably said antibodies being produced upon infection from a sample of biological fluid, preferably from a blood sample or a sample of blood components comprising the following steps:

- optionally incubating the sample to be tested with a buffer
- adding a solution containing said sample or mixture of the sample with the buffer on the reaction area of the in vitro device according to the invention,
- optionally reading before rinsing for sample load control;
- optionally depositing a rinse solution on the reaction area, and
- determining the presence of said antibodies by determining the presence of an antigen/antibody interaction, preferably if in the reaction area appears colored spot or determining the absence of said antibody by determining the absence of an antigen/antibody reaction, preferably if in the reaction area appears a colourless spot.

The incubating step may be performed in the presence of an agent capable of increasing reaction at a temperature between 4 and 40° C., for a period of between 3 and 60 min, preferably between 5 and 30 min. The skilled artisan would be able to determine the appropriate temperature depending on antibody or antigens to be detected and/or identified The buffer used in the incubating step is a buffer with molecule for increasing reaction.

The rinse solution used for rinsing the reaction area may be such as for example a hypertonic saline solution of stabilised pH between pH 6 and pH 8.5, preferably between pH 6.5 and pH 7.8, preferably between pH 7 and pH 7.5 and osmolarity between 300 mOsm and 800 mOsm. This solution can optionally contain detergents in low concentration (for example Tween 20 0.01 to 0.05% m/v).

The sample to be deposited can be biological fluid example: plasma, serum or total blood or blood components diluted or not in a buffer comprising a stabilised pH solution between pH 6 and pH 8.5, preferably between pH 6.5 and pH 7.8, in particular between pH 7 and pH 7.5 and osmolarity between 250 mOsm and 800 mOsm, preferably between 300 mOsm and 600 mOsm. This solution can optionally contain detergents in low concentration (for example Tween 20 0.01 to 0.05% m/v), saturation agents (especially BSA) and/or agents capable of potentializing antigen-antibody reactions. This buffer preferably has salinity less than 50 mM in NaCl.

If the plasma tested contains antibodies directed against the antigen present in the revelation agent, a colourless spot appears in the reaction area. A colourless centre means the absence or undetectable dose of antibodies directed against the antigen present in the revelation agent.

The revelation of antibody/antigen reaction is preferably performed by the use of colored beads or HRP (horseradish peroxidase) coupled to antibodies or molecule which would interact with the corresponding pathogen antigens.

The skilled artisan would be able to determine other means of labeling allowing to detect and/or to identify said antibody.

Reading the results can be visual or automatic.

DESCRIPTION OF THE FIGURES

FIG. 1 also shows scanning electron microscopy (SEM) view of section of the porous membrane comprising beads and antibodies fixed on their surface. b. Schema of the particular embodiment of the in vitro device of the invention, said device comprising a support on which is disposed the porous membrane including a hydrophilized reaction area on which are deposited several beads on which surface are fixed antibodies. The same layers as those shown on FIG. 1a are shown under the porous membrane.

EXAMPLES

Figure 1:
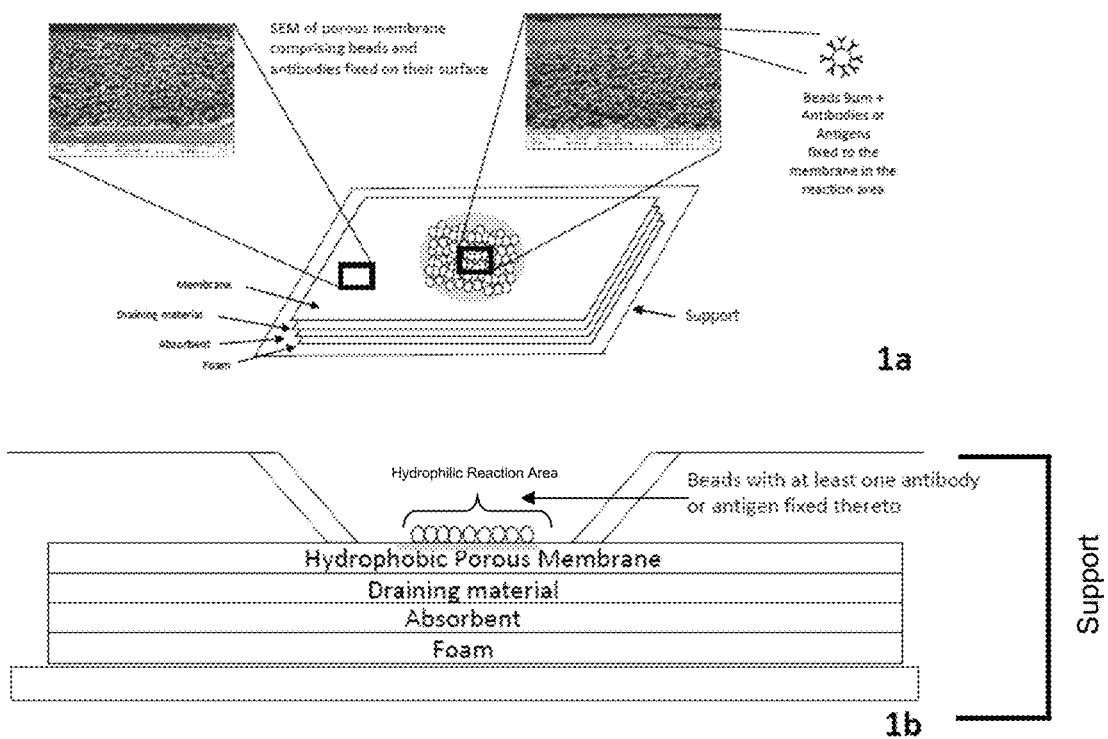
FIG. 1: a. Diagram of a particular embodiment of the in vitro device according to the invention viewed in perspective, said device comprising a porous membrane including a reaction area on which are deposited several beads having a size of 9 µm, on which surface are directly or indirectly fixed or adsorbed antibodies or antigens. Under the membrane are shown three layers, one of draining material, one of absorbent material and one of foam.

Example 1: Red Blood Cell Typing and Phenotyping in the In Vitro Device With Direct and Indirect Coupling of Anti-Red Blood Cells Antibodies on Beads Via Anti-Immunoglobulins IgM and IgG 1. Protocol for Preparing the In Vitro Device That Comprises on the Surface of the Reaction Area the Anti-Red Blood Cells Antibodies Directly Spotted on the Membrane 1.1. Materials for the Preparation of the In Vitro Device Membrane "POREX" 0.6 mm hydrophobic with 9 to 12 μm porosity; Cotton;
Cleanis;
Hydrophilization buffer (1% triton, 1% Green dye, phosphate buffered saline).
Wash Buffer (TLA composition);
Dilution buffer (Chromasolcoombs);
Antibodies (Anti-ABO01, Anti-ABO02, Anti-ABO03, Anti-RH1, Anti-RH2, Anti-RH3, Anti-RH4, Anti-RHS, Anti-KEL1, Negative Control).

1.2. Preparation Mode of the Reaction Medium

Deposit 1 μl of the hydrophilization solution in each well;
Drying 16 hours at 37° C. and 10% humidity;
Deposit 2 μl of antibody per well;
Drying 72 hours at 37° C. and 10% humidity.
Materials for the realization of the test are the reaction support, wash buffer and dilution buffer 1.3. Test Embodiment Dilute the pellet of red blood cells to 20% in the dilution buffer;
Deposit 20 μl of the suspension in the wells;
Incubate for 3 min at room temperature;
Deposit 80 μl of washing buffer;
Incubate 1 min at room temperature;
Deposit 80 μl of washing buffer.

2. Protocol for Preparing The In Vitro Device With Direct and Indirect Coupling of Anti-Red Blood Cells Antibodies on Beads Via Anti-Immunoglobulins IgM and IgG 2.1. Protocol for Direct Coupling of the anti-ABO01 (Anti-A), Anti-ABO02 (Anti-B) and Anti-ABO03 (Anti-AB) Antibodies to Latex Beads On 1 ml of homogenized 4% beads (Thermo Fisher latex Aldehyde/Sulfate beads 9 μm 4% w/v), 100 μl of 20× phosphate buffered saline are added and 2 ml of concentrated antibodies are dissolved. The volume is completed up to 4 ml with demineralized water. The solution is end over end mixed overnight to ensure coupling.

The excess active groups are blocked by suspending in the bead antibody solution 150 μl of 1M ethanolamine followed by a mixing for 2 hours at room temperature. The coupled beads are then washed extensively 2 times with 3 ml of conservation buffer (centrifugation 5 min at 2500 g before and after washes). Finally the bead pellet is resuspended in the conservation buffer to get back the introduced bead solution weight.

2.2. Anti-RH1, Anti-RH2, Anti-RH3, Anti-RH4, Anti-RH5 and Anti-KEL1 Antibodies Indirect Coupling Protocol On 1 ml of homogenized 4% beads, 200 μl of 20× phosphate buffered saline are added and 250 μl of 6D4 (anti human IgM, Diagast clone) at 1 mg/ml or 100 μl of C5-1 (anti human IgG, Diagast clone) at 3.69 mg/ml are dissolved. The volume is completed up to 4 ml with demineralized water. The solution is end over end mixed overnight to ensure coupling.

The excess active groups are blocked by suspending in the bead antibody solution 150 μl of 1M ethanolamine followed by a mixing for 2 hours at room temperature. The Anti-Human Globulin (AHG) coupled beads are then washed extensively 2 times with 3 ml of conservation buffer (centrifugation 5 min at 2500 g before and after washes). The bead pellet is resuspended with 2 ml of concentrated antibody plus 2 ml of phosphate buffered saline. The solution is end over end mixed overnight to ensure coupling.

The resulting beads are then washed extensively 2 times with 3 ml of conservation buffer (centrifugation 5 min at 2500 g before and after washes). Finally the bead pellet is resuspended in the conservation buffer to get back the introduced bead solution weight. The negative control beads are directly saturated with ethanolamine.

The antibodies clones used in the Examples are shown in Table 4 below:

TABLE 4

Antibody clones used in the Examples.

| Clone | Antigen | Is | Specie | Coupling type |
|---|---|---|---|---|
| 9113D1 | ABO01 | Ig | mouse | Direct |
| 9621 | ABO02 | Ig | mouse | Direct |
| 152D12 | ABO03 | Ig | mouse | Direct |
| P3X255 | RH2 | Ig | human | indirect through |
| RH3 | RH3 | Ig | human | indirect through |
| RH4 | RH4 | Ig | human | indirect through |
| P3GD5 | RH5 | Ig | human | indirect through |

TABLE 4-continued

Antibody clones used in the Examples.

| Clone | Antigen | Is | Specie | Coupling type |
|---|---|---|---|---|
| K601 | KEL1 | Ig | human | indirect through |
| P3X212 | RH1 | Ig | human | indirect through |
| 6D4 | AHG | Ig | mouse | Direct |
| C51 | AHG | Ig | mouse | Direct |

The antibody clones in Table 4 are clones performed and sold by the Applicant (Diagast, France).

2.3. Reaction Device Preparation and Detection Procedure

The device is a moulded plastic cassette in which a Porex HDPE hydrophobic membrane of 0.6 mm thickness and porosity between 9 to 12 µm, a draining pad (NA7150 PES from Subrenat) and an absorbent pad (Cleanis) are assembled.

The porous membrane is hydrophilized with 0.5 µl of a surfactant solution (phosphate buffered saline supplemented with 0.5% Triton X-100; 0.5% green dye and 0.13M saccharose) and potentially dried for 1 hour at 37° C., 10% humidity. 5 µl of antibody or negative control coupled beads at 4% are then spotted and the device is dried for 1 hour at 37° C., 10% humidity before immediate use or extended conservation.

A test is initiated by diluting red blood cells at 5% in Chromasolcoombs (Diagast formulation) and 10 µl are introduced in each well followed by two 30 µl washes (phosphate buffered saline supplemented with 0.2% Tween20 and 0.54% green dye).

In this example, the Applicant also compared the in vitro device containing anti-red blood cells antibodies coupled to beads for the blood grouping and phenotyping prepared by the above described protocol to an in vitro device in which the anti-red blood cells antibodies are directly spotted on the porous membrane (similar to those described in WO2013/186482).

3. Results

Figure 2:
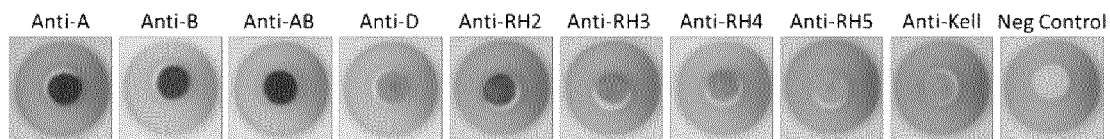
FIG. 2: Comparative tests of detection of red blood cell antigens with Anti-ABO01, Anti-ABO02, Anti-ABO03, Anti-RH1, Anti-RH2, Anti-RH3, Anti-RH4, Anti-RH5, Anti-KEL1 and Negative Control by the in vitro device as those described in WO2013/186482 (FIG. 2a) and the in vitro device of the present invention (FIG. 2b).
Figure 2:
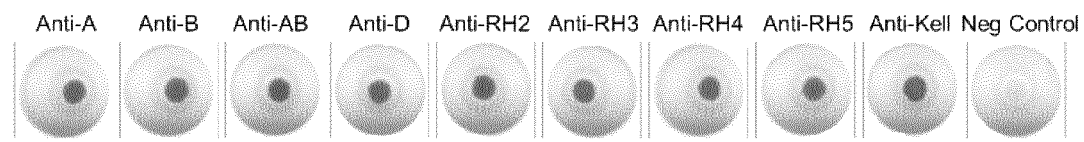

The obtained comparative results are shown on FIG. 2, wherein the presence of a dark gray spot (corresponding to red spot in the color version) indicates an immune complex formation, and therefore a positive reaction (presence of the antigen at the red blood cell surface), while the presence of a colourless spot reflects a negative reaction (absence of the antigen at the red blood cell surface).

It appears from FIG. 2 that antibodies of blood groups anti-ABO01, anti-ABO02, anti-ABO03, anti-RH1, anti RH2, anti-RH3 anti-RH4 anti RH5 and anti-KEL1 fixed directly or indirectly on the bead surface bind the corresponding antigens present on the surface of red blood cells of the tested samples in specific manner. Indeed, the surface of the spot where the beads were deposited remains well colored in red which indicates that the antibodies of red blood cells are not adsorbed by the porous membrane which allows specific and sensitive detection of red blood cells antigens (FIG. 2b).

It can be seen from FIG. 2a that in the in vitro device without beads the reactions with some antibodies, particularly Anti-RH1, Anti-RH3, Anti-RH4, Anti-RH5 and Anti-KEL1 antibodies have low sensitiveness (very low intensity of dark grey).

When comparing the results on FIG. 2b obtained with the in vitro device of the invention to those of FIG. 2a obtained with the in vitro device without bead, it appears that the greys pots for antibodies Anti-RH1, Anti-RH3, Anti-RH4, Anti-RH5 and Anti-KEL1KEL1 are much more visible on FIG. 2a than those of FIG. 2a, which demonstrates that the in vitro device of the invention allows to obtain a more sensitive detection of the most anti-red blood cells antigens.

Example 2: Indirect Coupling of Red Blood Cells Antibodies Via Affinity Proteins for Antibodies

1. Indirect Antibodies Coupling

On 1 ml of homogenized 4% latex beads (Thermo Fisher latex Aldehyde/Sulfate 9 µm 4% w/v), 5 or 2.5 µg of Protein AGL are dissolved in 3 ml PBS1× and are added. The solution is end over end mixed overnight to ensure coupling.

On 1 ml of centrifugated 4% beads (Thermo Fisher latex Aldehyde/Sulfate 9 µm 4% w/v) coupled with protein AGL, 3 ml of 1× phosphate buffered saline are added and 1 ml of Anti-ABO01 antibody (91 13 D10 Diagast clone) or Anti-ABO02 antibody (96 21 A8 Diagast clone) or Anti-ABO03 (152D12 Diagast clone) are dissolved. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

2. Reaction Device Preparation and Detection Procedure

The device is a moulded plastic cassette in which a Porex HDPE hydrophobic membrane of 0.6 mm thickness and porosity between 9 to 12 µm, a draining pad (9610HY) and an absorbent pad (Cleanis) are assembled.

The porous membrane is hydrophilized with 0.5 µl of a surfactant solution (phosphate buffered saline supplemented with 2% Triton X-100 and 1% of green dye). 2 µl of antibody coupled beads at 2%, are then spotted. The device is dried for 15 min at 37° C., 20% humidity before use.

The detection procedure is initiated by introducing in each well 50 µl of red blood cells diluted at 1.5% in PBS1× supplemented with 0.00625% Tween20.

A first image before washes is acquired. The reaction zone is then washed with 30 µl of phosphate buffered saline supplemented with 0.2% Tween-20. An image is acquired after wash.

3. Results

Figure 3:
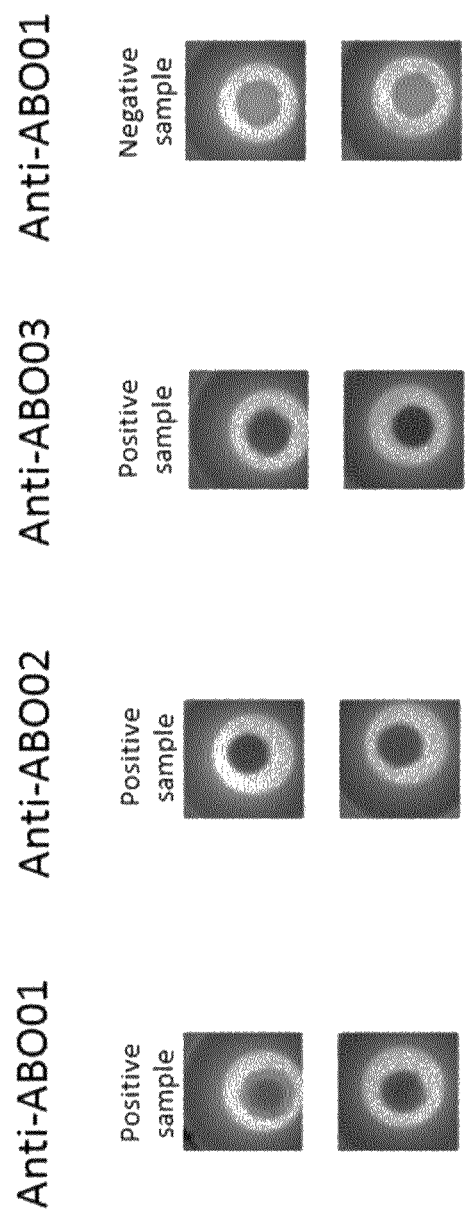
FIG. 3: Detection of red blood cell ABO01, ABO02 and ABO3 antigens by IgM antibody indirectly fixed on latex beads via the protein on the protein A/G/L.

FIG. 3 shows the resulting image on which is observed the presence of dark grey spots (corresponding to the red spot in color image) indicating an immune complex formation and therefore a positive reaction, while the presence of a colorless spot reflects a negative reaction.

Example 3: Coupling of Antibodies of Red Blood Cells on Beads Having Different Chemical Functional Groups on Their Surface and Different Size in Different Reactional Conditions

1. Chloromethyl Group

1.2. Antibodies Coupling

On 500 µl of homogenized chloromethyl beads (Thermo Fisher chloromethyl latex beads 4% w/v, 2.0 µm) 1.5 ml of phosphate buffer is added and the obtained solution is centrifuged at 3000 g for 20 min. The supernatant is discarded and the bead pellet is then resuspended with a mix of 950 μl of phosphate buffered saline and 50 μl of concentrated CPC51 or CP6D4 (Diagast AHG). The antibody bead solution is incubated overnight at room temperature on a tube rocker.

After AHG chemical coupling, the bead solution is centrifuged at 3000 g for 15 min and the supernatant is discarded. The beads are washed with 1.5 ml of phosphate buffered saline and the solution is centrifuged at 3000 g for 10 min. The supernatant is discarded and the excess active groups are blocked by adding 1 ml of 1M ethanolamine before mixing for 20 min at room temperature. The AHG coupled bead solution is centrifuged at 3000 g for 20 min before washing with 1.5 ml of phosphate buffer saline. 1 ml of concentrated anti-A (Anti-ABO1) antibodies (clones IgM 91 13 D10 or IgG 162 47 (3) E6 both Diagast clones) is dissolved on the bead pellet and the solution is mixed for two hours at room temperature before centrifugation and wash with 1.5 ml of phosphate buffered saline. Finally the bead pellet is resuspended in the conservation buffer to get back the introduced bead solution weight.

1.2. Reaction Device Preparation and Detection Procedure

The device is a moulded plastic cassette in which a Porex HDPE hydrophobic membrane of 0.6 mm thickness and porosity between 9 to 12 μm, a draining pad (cotton wool from Alan&co) and an absorbent pad (Cleanis) are assembled.

The porous membrane is hydrophilized with 2.5 μl of a surfactant solution (filtered water supplemented with 1% Triton X-100) and 20 μl (FIGS. 4A and 4C) or 10 μl (FIGS. 4B and 4D) of antibody coupled beads at 4% are then spotted. The device is let to stand 30 min at room temperature before use.

The detection procedure is initiated by introducing in each well 13 μl of a mix of 30 μl of red blood cells at 10% in chromasolcoombs (Diagast formulation) and 10 μl of an hexadimethrine bromide solution.

The reaction zone is washed twice with 25 μl of phosphate buffered saline supplemented with 0.1% Tween-20.

1.3. Results

Figure 4:
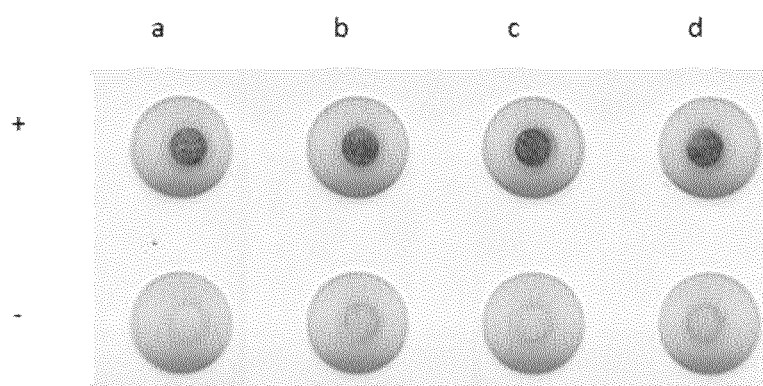
FIG. 4: a and b: Detection of red blood cell ABO01 antigen by an IgM antibody bound to AHG (anti-human globulin)-coupled to chloromethyl latex beads with two different volumes of antibodies-coupled bead loaded on the membrane (a: 20 µl and b: 10 µl). c and d: Detection of red blood cell ABO01 antigen by an IgG antibody bound to AHG coupled chloromethyl latex beads with two different volumes of antibodies-coupled bead loaded on the membrane (c: 20 µl and d: 10 µl).

FIG. 4 shows the resulting image on which is observed the presence of dark gray spot (corresponding to a red spot in color image) indicating an immune complex formation (group A red blood cells), and therefore a positive reaction, while the presence of a colourless spot reflects a negative reaction (group B red blood cells).

2. Epoxide Group

2.1. Antibodies Coupling 0.5 g of epoxide resin (Biorad Profinity epoxide resin, supplied as a dry powder, particle size 45-90 microns) are weighted out and swelled in 50 ml of phosphate buffered saline for 30 min under gentle agitation. Beads expand to 5 ml which give a solution at approximately 10%.

Beads are centrifuged at 2500 g for 5 min, the supernatant is discarded and the pellet is resuspended in 4.5 ml of phosphate buffered saline then centrifuged again.

360 μl of concentrated anti IgM AHG (CP6D4 Diagast) are dissolved in 12 ml of phosphate buffered saline and the mix is added on the bead pellet for coupling. The antibody bead solution is incubated 1H30 at room temperature on a rotary shaker.

After AHG chemical coupling, the bead solution is centrifuged at 2500 g for 5 min and the supernatant discarded. The beads are washed with 4.5 ml of phosphate buffered saline and the solution is centrifuged at 2500 g for 5 min. The supernatant is discarded and the excess active groups are blocked by adding 3 ml of 1M ethanolamine before mixing for 45 min at room temperature. The AHG coupled bead solution is centrifuged at 2500 g for 5 min before washing with 4.5 ml of phosphate buffered saline.

300 μl of anti-RH2, anti-RH3, anti-RH4 or anti-RH5 (respectively P3X255 13 G8 Diagast clone, RH3 906 Diagast clone, MS33 Millipore clone and P3GD C512 Diagast clone) are diluted in 2200 μl of phosphate buffered saline and added on the AHG coupled beads. For anti-Kell antibody 1500 μl are diluted in 1000 μl of phosphate buffered saline and for negative control 2500 μl of phosphate buffered saline. Obtained solution is mixed for 45 min at room temperature before centrifugation and wash. Finally the bead pellet is resuspended in phosphate buffered saline supplemented with conservatives to get back a 50% solution of coupled beads.

2.2. Reaction Device Preparation and Detection Procedure

The device is a moulded plastic cassette in which a Porex HDPE hydrophobic membrane of 0.6 mm thickness and porosity between 9 to 12 μm, a draining pad (cotton wool from Alan&co) and an absorbent pad (Cleanis) are assembled.

The porous membrane is hydrophilized with 1 μl of a surfactant solution (filtered water supplemented with 1% Triton X-100) and dried overnight at room temperature. 10 μl of antibody coupled beads at 50% are then spotted. The device is let to stand 30 min at room temperature before use.

The detection procedure is initiated by introducing in each well 10 μl of undiluted red blood cells. The reaction zone is washed twice with 40 μl of a phosphate buffered saline supplemented with 0.2% Tween-20 and preservatives.

2.3. Results

Figure 5:
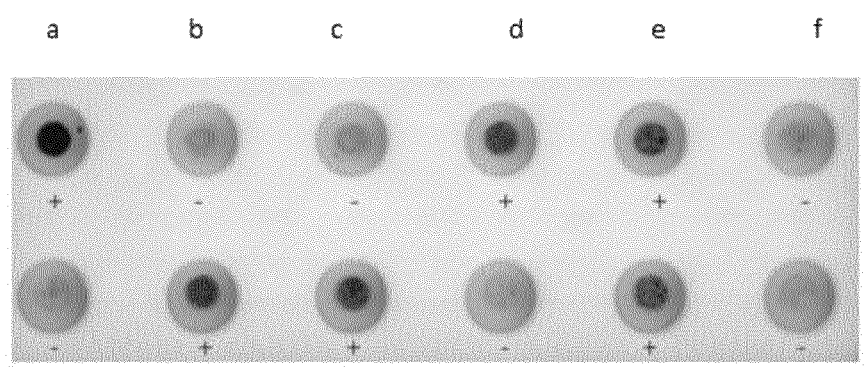
FIG. 5: Detection of red blood cell antigens with IgM specific antibody bound to AHG coupled epoxide beads. (a: RH2; b: RH3; c: RH4; d: RH5; e: KEL1 antigens and f: negative control)

FIG. 5 shows the resulting image on which is observed the presence of a dark gray spot (corresponding to a red spot in the color image) indicating an immune complex formation, and therefore a positive reaction, while the presence of a colourless spot reflects a negative reaction. Whatever the red blood cell phenotype, the negative control results in a colourless spot.

3. N-Hydroxysuccinimide (NHS) Group

3.1. Antibodies Coupling 1 ml of NHS Beads (Pierce™ NHS-Activated Agarose Slurry) are diluted with 5 ml of phosphate buffered saline and centrifuged at 2500 g for 5 min, the supernatant is discarded and the pellet is resuspended in 4.5 ml of phosphate buffered saline for 3 additional washes.

2 ml of concentrated anti IgG AHG (C51 Diagast) are dissolved in 3 ml of phosphate buffered saline and the mix is added on the bead pellet for coupling. The antibody bead solution is incubated one hour and a half at room temperature on a rotary shaker.

After AHG chemical coupling, the bead solution is centrifuged at 2500 g for 5 min and the supernatant discarded. The beads are washed with 4.5 ml of phosphate buffered saline and the solution is centrifuged at 2500 g for 5 min. The supernatant is discarded and the excess active groups are blocked by adding 3 ml of 1M ethanolamine before mixing for 45 min at room temperature. The AHG coupled bead solution is centrifuged at 2500 g for 5 min before washing with 4.5 ml of phosphate buffered saline.

10 ml of anti-RH1 and anti-FY1 antibodies (respectively HM16 and F655 Diagast clones) are added on the AHG coupled beads. Obtained solution is mixed for 1 hour at room temperature before centrifugation and washing. Finally the bead pellet is resuspended in phosphate buffered saline supplemented with conservatives to get a 50% solution of coupled beads.

3.2. Reaction Device Preparation and Detection Procedure

Figure 6:
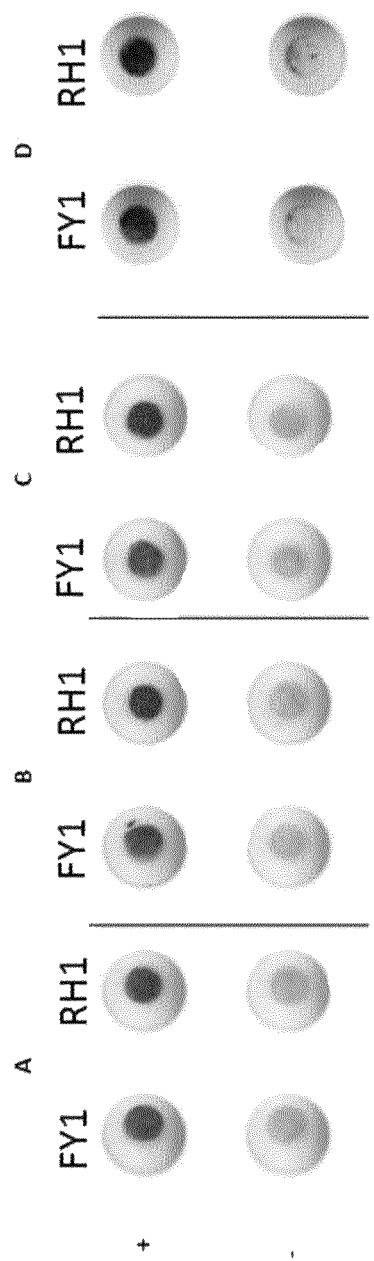
FIG. 6: Detection of FY1 and RH1 red blood cell antigens by IgG specific antibodies bound to AHG (Anti-Human globulin) coupled NHS agarose beads in the conditions described in Example 3. a. b. and c. represent different detection procedures and d. different reaction device and detection procedure.

The device presented on FIGS. 6 (A, B and C) is a moulded plastic cassette in which a Porex HDPE hydrophobic membrane of 0.6 mm thickness and porosity between 9 to 12 µm, a draining pad (cotton wool from Alan&co) and an absorbent pad (Cleanis) are assembled.

The porous membrane is hydrophilized with 2.5 µl of a surfactant solution (filtered water supplemented with 1% Triton X-100) and dried overnight at 37° C. 20 µl of antibody coupled beads at 50% are then spotted. The device is let to stand 30 min at room temperature before use.

FIG. 6A: The detection procedure is initiated by introducing in each well 7 µl of red blood cells diluted at 25% in an 0.25% hexadimethrine bromide solution. The reaction zone is washed with 20 µl+30 µl of phosphate buffered saline supplemented with 0.01% Tween-20.

FIG. 6B: The detection procedure is initiated by introducing in each well 5 µl of red blood cells diluted at 25% in an 0.3% hexadimethrine bromide solution. The reaction zone is washed with 20 µl+30 µl of phosphate buffered saline supplemented with 0.01% Tween-20.

FIG. 6C: The detection procedure is initiated by introducing in each well 5 µl of red blood cells diluted at 25% in an 0.4% hexadimethrine bromide solution. The reaction zone is washed with 20 µl+30 µl of phosphate buffered saline supplemented with 0.01% Tween-20.

The device presented on FIG. 6D is a moulded plastic cassette in which a Lydall UHMWPE hydrophobic membrane of 105 µm thickness and porosity of 12 µm (Solupor 70M01A), a draining pad (cotton wool from Alan&co) and an absorbent pad (Cleanis) are assembled.

The porous membrane is hydrophilized with 2 µl of a surfactant solution (filtered water supplemented with 1% Triton X-100) and dried for 1 hr 30 min at 37° C. 20 µl of antibody coupled beads at 50% are then spotted. The device is let to stand 30 min at room temperature before use.

The detection procedure is initiated by introducing in each well 7 µl of red blood cells diluted at 25% in an 0.25% hexadimethrine bromide solution. The reaction zone is washed with 30 µl+50 µl of phosphate buffered saline supplemented with 0.01% Tween-20 and additional 20 µl of phosphate buffered saline supplemented with 0.1% Tween-20 and 0.007% Triton X-100.

3.3. Results

On FIG. 6 from the resulting image is observed the presence of a dark gray spot (corresponding to a red spot in color image) indicating an immune complex formation, and therefore a positive reaction (detection of RH1 or FY1 antigen), while the presence of a colourless spot reflects a negative reaction.

Example 4: Concentration of the Beads

The aim of this experience is to test different concentrations of beads to be deposited on the porous membrane.

1. Antibodies Coupling

On 1 ml of homogenized 4% beads (Thermo Fisher latex Aldehyde/Sulfate 9 µm 4% w/v), 100 µl of 20× phosphate buffered saline are added and 2 ml of affinity purified anti-ABO02 antibody (96 21 A8 Diagast clone) are dissolved. The volume is completed up to 4 ml with demineralized water. The solution is end over end mixed overnight to ensure coupling.

The excess active groups are blocked by suspending in the bead antibody solution 150 µl of 1M ethanolamine and mixed for 2 hours at room temperature. The coupled beads are then washed extensively 2 times with 3 ml of conservation buffer (centrifugation 5 min at 2500 g before and after washes). Finally the bead pellet is resuspended in the conservation buffer to get back the introduced bead solution weight.

2. Reaction Device Preparation and Detection Procedure

The device is a moulded plastic cassette in which a Porex HDPE hydrophobic membrane of 0.6 mm thickness and porosity between 9 to 12 µm, a draining pad (cotton wool from Alan&co) and an absorbent pad (Cleanis) are assembled.

The porous membrane is hydrophilized with 1 µl of a surfactant solution (phosphate buffered saline supplemented with 1% Triton X-100 and 1% of green dye). 10 µl of antibody coupled beads, concentration between 1 to 5%, are then spotted. The device is dried for 15 min at 37° C., 20% humidity before use.

The detection procedure is initiated by introducing in each well 50 µl of red blood cells diluted at 0.15% in Chromasolcoombs supplemented with 0.00625% Tween20. The reaction zone is washed one or two times with 30 µl of phosphate buffered saline supplemented with 0.2% Tween-20.

3. Results

Figure 7:
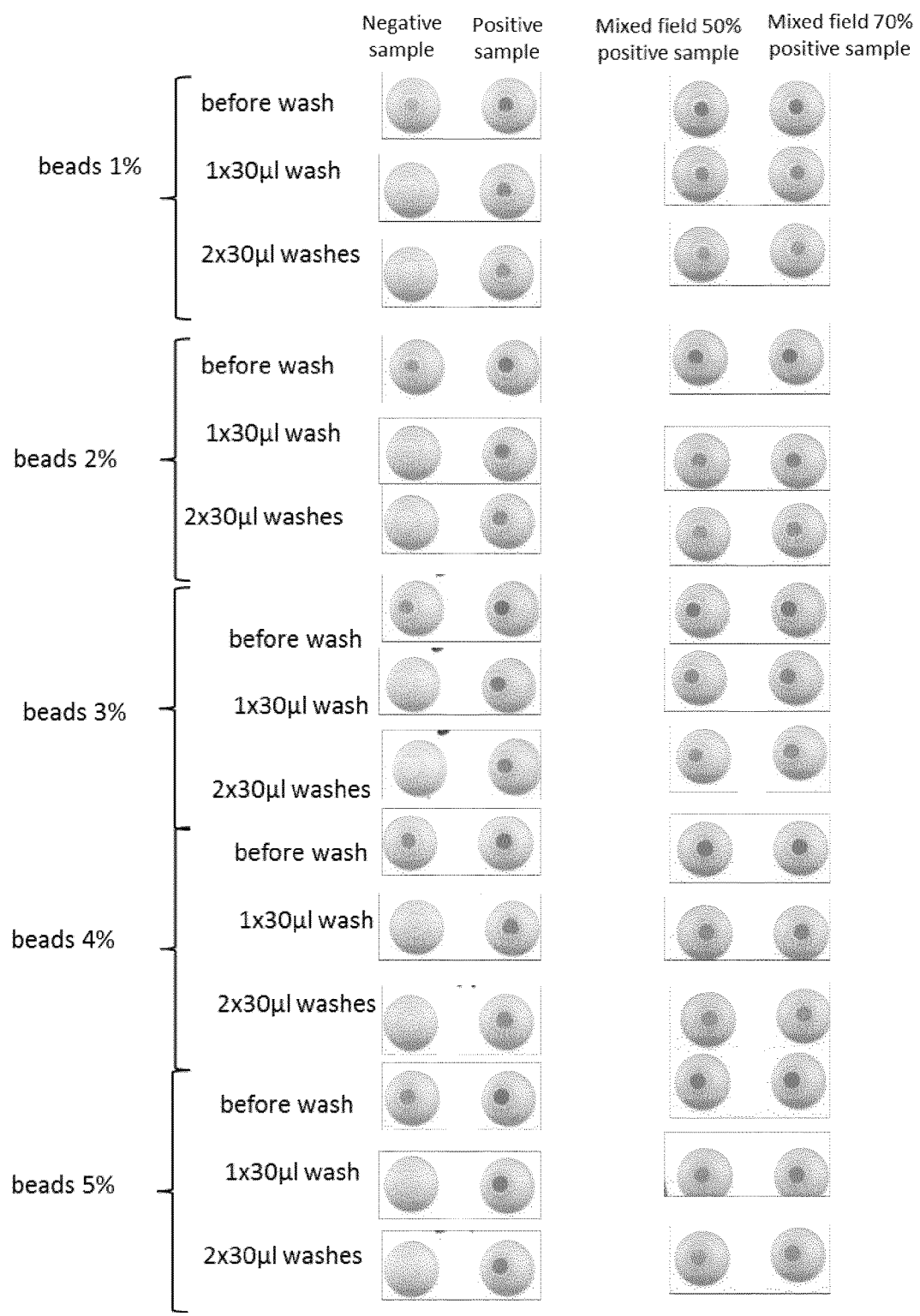
FIG. 7: Detection of red blood cell ABO02 antigens and of mixed filed populations with different amounts (1 to 5%) of anti-ABO02 coupled to aldehyde 9 µm latex beads loaded on the porous membrane.

FIG. 7 shows the resulting image on which is observed the presence of dark gray spots (corresponding to the red spot in color image) indicating an immune complex formation, and therefore a positive reaction (group ABO02 red blood cells), while the presence of a colourless spot reflects a negative reaction. The specificity and sensitivity are respected for a bead concentration going from 1 to 5%, after one or two washes. Mixed field blood cells are detectable through a decrease in intensity compared to the signal of a 100% positive population.

Example 5: Thickness of Porous Hydrophobic Membrane

1. Antibodies Coupling

1.1. Anti-ABO01 Coupling

On 1 ml of homogenized 4% beads (Thermofisher latex Aldehyde/Sulfate 9 µm 4% w/v), 100 µl of 20× phosphate buffer are added and 2 ml of affinity purified anti-ABO01 (25 21 B8 Diagast clone) antibody are dissolved. The volume is completed up to 4 ml with demineralized water. The solution is end over end mixed overnight to ensure coupling.

The excess active groups are blocked by suspending in the bead antibody solution 150 µl of 1M ethanolamine and mixed for 2 hours at room temperature. The coupled beads are then washed extensively 2 times with 3 ml of conservation buffer (centrifugation 5 min at 2500 g before and after washes). Finally the bead pellet is resuspended in the conservation buffer (phosphate buffered saline supplemented with 0.5% bovine serum albumin and 0.25M saccharose) to get back the introduced bead solution weight.

1.2. Anti-RH2, Anti-RH5 and Anti-KEL1 Coupling

On 1 ml of homogenized 4% beads, 200 µl of PBS20× are added and 250 µl of 6D4 (anti human IgM) for anti-RH2 and anti-RH5 (respectively P3x255 13 G8 and P3GD C512 Diagast clones) at 1 mg/ml or 100 µl of C5-1 (anti human IgG) for anti-KEL1 (601 Diagast clone) at 3.5 mg/ml are dissolved. The volume is completed up to 4 ml with demineralized water. The solution is end over end mixed overnight to ensure coupling.

The excess active groups are blocked by suspending in the bead antibody solution 150 µl of 1M ethanolamine and mixed for 2 hours at room temperature. The AHG coupled beads are then washed extensively 2 times with 3 ml of conservation buffer (centrifugation 5 min at 2500 g before and after washes). The bead pellet is resuspended with 2 ml of concentrated antibody plus 2 ml of phosphate buffer. The solution is end over end mixed overnight to ensure coupling.

The coupled beads are then washed twice with 3 ml of conservation buffer (centrifugation 5 min at 2500 g before and after washes). Finally the bead pellet is resuspended in the conservation buffer (phosphate buffered saline supplemented with 0.5% bovine serum albumin and 0.25M saccharose) to get back the introduced bead solution weight.

1.3. Reaction Device Preparation and Detection Procedure

Figure 8:
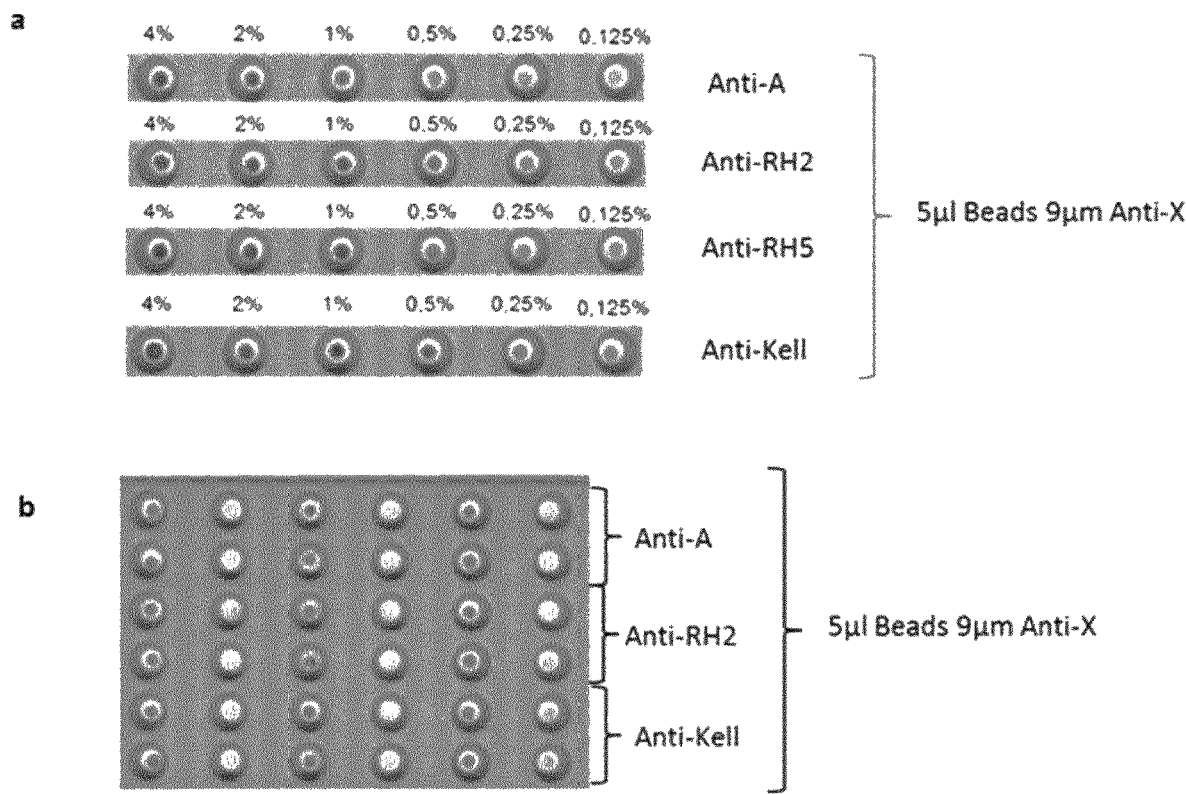
FIG. 8: a. Detection of ABO01, RH2, RH5 and KEL1 red blood cell antigens by different amounts of specific antibodies-coupled to aldehyde 9 µm latex beads (0.125 to 4%) on a device comprising a 1.5 mm thickness membrane. b. Detection of ABO01, RH2 and KELl1 red blood cell antigens by specific antibodies coupled to aldehyde 9 µm latex beads (4%) on a device comprising a 0.6 mm thickness membrane.

The device shown on FIG. 8a is a moulded plastic cassette in which a Porex HDPE hydrophobic membrane of 1.5 mm thickness and porosity between 7 to 12 µm, a draining pad (cotton wool from Alan&co) and an absorbent pad (Cleanis) are assembled.

The porous membrane is hydrophilized with 1 µl of a surfactant solution (phosphate buffered saline supplemented with 3% Triton X-100, 0.26M Saccharose and 1% of green dye). The device is dried a first time for 1 hour at 37° C., 10% humidity. 5 µl of antibody coupled beads, concentration between 0.125 to 4%, are then spotted. The device is dried a second time for 1 hour at 37° C., 10% humidity before use.

The detection procedure is initiated by introducing in each well 10 µl of red blood cells diluted at 5% in physiological water. The reaction zone is washed with 100 µl phosphate buffered saline supplemented with 0.1% Tween-20 and 0.007% Triton X-100.

The device shown on FIG. 8b is a moulded plastic cassette in which a Porex HDPE hydrophobic membrane of 0.6 mm thickness and porosity between 9 to 12 µm, a draining pad (NA7300PES from Subrenat) and an absorbent pad (Cleanis) are assembled.

The porous membrane is hydrophilized with 0.5 µl of a surfactant solution (phosphate buffered saline supplemented with 0.5% Triton X-100, 0.13M Saccharose and 0.5% of green dye). The device is dried a first time for 1 hour at 37° C., 10% humidity. 5 µl of antibody coupled beads at 4%, are then spotted. The device is dried a second time for 1 hour at 37° C., 10% humidity before use.

The detection procedure is initiated by introducing in each well 10 µl of red blood cells diluted at 5% in physiological water. The reaction zone is washed with 100 µl of phosphate buffered saline supplemented with 0.1% Tween-20 and 0.007% Triton X-100.

1.4. Results

The presence of a dark grey spot (a red spot) on FIG. 8a indicates an immune complex formation and therefore a positive reaction. The sensitivity is respected for a bead concentration going from 4 to 0.125% with a decrease in intensity.

The presence of a dark grey spot (a red spot) on FIG. 8b indicates an immune complex formation, and therefore a positive reaction, while the presence of a colourless spot reflects a negative reaction.

Example 6: Type and Concentration of Surfactant Used For Hydrophilizing the Porous Membrane 1. Anti-ABO01 Coupling On 1 ml of homogenized 4% beads (Thermo Fisher latex Aldehyde/Sulfate 9 µm 4% w/v), 100 µl of 20× phosphate buffered saline are added and 1 ml of affinity anti-ABO01 antibody (25 21 B8 Diagast clone) is dissolved. The volume is completed up to 4 ml with demineralized water. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

2. Reaction Device Preparation And Detection Procedure

The device is a moulded plastic cassette in which a Porex HDPE hydrophobic membrane of 0.6 mm thickness and porosity between 9 to 12 µm, a draining pad (cotton wool from Alan&co) and an absorbent pad (Cleanis) are assembled.

The porous membrane is hydrophilized with 1 µl of a surfactant solution listed above
  a. 1.5% Triton X-100
  b. Polyoxyethylene 10%
  c. Nonyl-β-D glucoside 50 mM 10 µl of antibody coupled beads, concentration at 3% are then spotted. The detection procedure is initiated by introducing in each well 50 µl of red blood cells diluted at 1.5% in phosphate buffered saline supplemented with 0.00625% Tween-20. The reaction zone is washed with 30 µl phosphate buffered saline supplemented with 0.2% Tween-20.

3. Results

Figure 9:
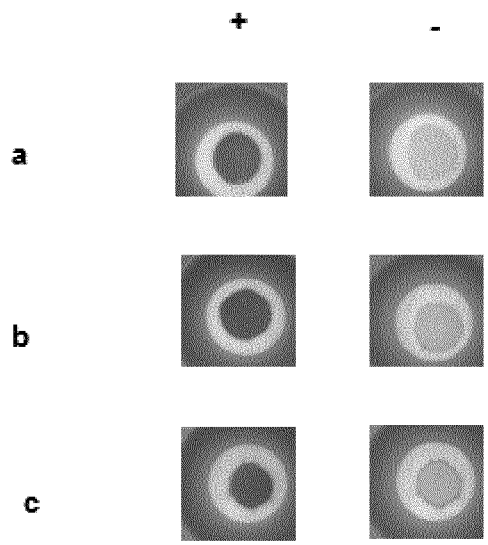
FIG. 9: Detection of red blood cell ABO1 antigen by specific antibodies coupled to aldehyde 9 µm latex beads loaded on an in vitro device comprising a 0.6 mm thickness membrane hydrophilized with a. Triton X-100 b. polyoxyethylene and c. nonyl B D glucoside.

FIG. 9 shows the resulting image on which is observed the presence of dark grey spots (corresponding to the red spot in color image) indicating an immune complex formation and therefore a positive reaction, while the presence of a colourless spot reflects a negative reaction. The specificity is respected whatever the surfactant used.

Example 7: Absorbing and Draining Material Used in the Device of the Invention

1. Absorbing Material

1.1. Antibodies Coupling

On 1 ml of homogenized 4% beads, 200 µl of 20× phosphate buffered saline are added and 250 µl of 6D4 (anti human IgM Diagast clone) are dissolved. The volume is completed up to 4 ml with demineralized water. The solution is end over end mixed overnight to ensure coupling.

The excess active groups are blocked by suspending in the bead antibody solution 150 µl of 1M ethanolamine and mixed for 2 hours at room temperature. The AHG coupled beads are then washed extensively 2 times with 3 ml of conservation buffer (centrifugation 5 min at 2500 g before and after washes). The bead pellet is resuspended with 2 ml of concentrated anti RH2 antibody (P3X255 13 G8 Diagast clone) plus 2 ml of phosphate buffered saline. The solution is end over end mixed overnight to ensure coupling.

The coupled beads are then washed extensively 2 times with 3 ml of conservation buffer (centrifugation 5 min at 2500 g before and after washes). Finally the bead pellet is resuspended in the conservation buffer to get back the introduced bead solution weight.

1.2. Reaction Device Preparation and Detection Procedure

The device is a moulded plastic cassette in which a Porex HDPE hydrophobic membrane of 0.6 mm thickness and porosity between 9 to 12 µm, a draining pad (NA7150 PES from Subrenat) and an absorbent pad (references from Mc Arlaid below) are assembled.

Figure 10:
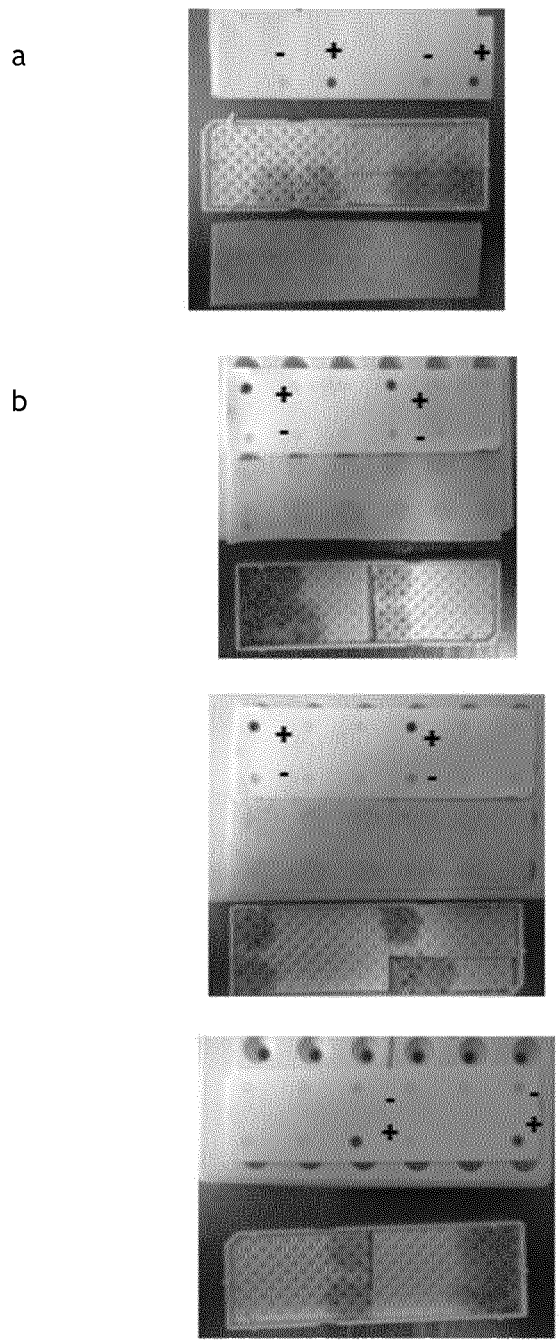
FIG. 10: a. Detection of red blood cell RH2 antigen by specific antibodies coupled on aldehyde 9 µm latex beads on a device comprising a T-499 (left) or SCP-300-TCF (right) as absorbent. b. Detection of red blood cell RH2 antigen by specific antibodies coupled to aldehyde/sulfate 9 µm latex beads on a device comprising a T-099 (left) or T-499 (right) as absorbent. c. Detection of red blood cell RH2 antigen by specific antibodies coupled on aldehyde/sulfate 9 µm latex beads on a device comprising a T-499 (left) or T-183-5 (right) as absorbent. d. Detection of red blood cell RH2 antigen by specific antibodies coupled to aldehyde/sulfate 9 µm latex beads on a device comprising a T-499 (left) or SCP-200-TCF (right) as absorbent. For each image the device is shown disassembled; from top to bottom: membrane on plastic device and absorbent.

The used adsorbing material is as follows:
T-499 or SCP-300 TCF (FIG. 10a)
T-099 or T-499 (FIG. 10b)
T-499 or T-183-5 (FIG. 10c)
T-499 or SCP-200-TCF (FIG. 10d)

The porous membrane is hydrophilized with 1 µl of a surfactant solution (phosphate buffered saline supplemented with 0.5% Triton X-100; 1% green dye). 10 µl of antibody or negative control coupled beads at 1% are then spotted and the device is dried for 15 min at 37° C., 20% humidity before immediate use or extended conservation.

A test is initiated by diluting red blood cells at 2.5% in chromasolcoombs (Diagast formulation) and 50 µl are introduced in each well followed by two times 30 µl of washing buffer (phosphate buffered saline supplemented with 0.2% Tween20).

1.3. Results

It appears from FIG. 10a, b, c and d that any of the tested absorbent layer could guarantee the detection of RH2 positive red blood cell (presence of a red spot, visible as dark gray spots). The specificity is respected; an uncolored spot reflects an RH2 negative red blood cell.

2. Draining Materials

2.1. Antibodies Coupling

On 1 ml of homogenized 4% beads, 1 ml of concentrated anti-AB antibody (152 D12 Diagast clone) is dissolved. The volume is completed up to 4 ml with phosphate buffered saline. The solution is end over end mixed overnight to ensure coupling.

The coupled beads are then washed extensively 2 times with 3 ml of conservation buffer (centrifugation 5 min at 2500 g before and after washes). Finally the bead pellet is resuspended in the conservation buffer to get back the introduced bead solution weight.

2.2. Reaction Device Preparation and Detection Procedure

The device is a moulded plastic cassette in which a Porex HDPE hydrophobic membrane of 0.6 mm thickness and porosity between 9 to 12 µm, a draining pad (references below) and an absorbent pad (Cleanis) are assembled.

The draining material is as follows:
cotton wool (from Alan &co), shown on FIG. 11a
NT 9750 HY (from Subrenat), shown on FIG. 11b,
NT 9610 HY (from Subrenat), shown on FIG. 11c The porous membrane is hydrophilized with 1 µl of a surfactant solution (phosphate buffered saline supplemented with 1% Triton X-100; 1% green dye). 10 µl of antibody or negative control coupled beads at 1% are then spotted and the device is dried for 15 min at 37° C., 10% humidity before immediate use or extended conservation.

A test is initiated by diluting red blood cells at 2.5% in chromasolcoombs (Diagast formulation) and 50 µl are introduced in each well followed by two 30 µl washes (phosphate buffered saline supplemented with 0.2% Tween20).

2.3. Results

Figure 11:
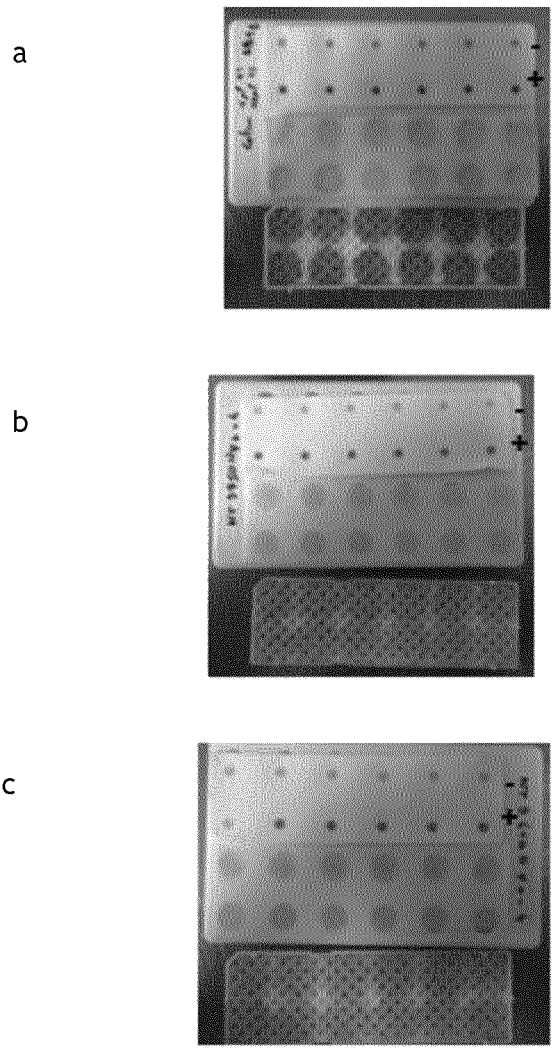
FIG. 11: a. Detection of red blood cell ABO02 antigen by anti-ABO03 antibody coupled to aldehyde 9 µm latex beads on a device comprising cotton wool as draining pad. b. Detection of red blood cell ABO02 antigen by anti-ABO03 antibody coupled to aldehyde/sulfate 9 µm latex beads on a device comprising NT 9750 HY as draining pad. C. Detection of red blood cell ABO02 antigen by anti-ABO03 antibody coupled on aldehyde/sulfate 9 µm latex beads on a device comprising NT 9610 HY as draining pad. For each image, the device is shown disassembled; from top to bottom: membrane, draining pad and absorbent.

FIG. 11 shows that any of the draining pad could guarantee the detection of B positive red blood cell (presence of a red spot visible as dark gray spot on the figure). The specificity is respected; an uncolored spot is obtained with O red blood cells.

Example 8: Grouping and Detection of Mixed Field Population Using the Device of the Invention

1. Antibodies Coupling

On 1 ml of homogenized 4% beads (Thermo Fisher latex Aldehyde/Sulfate 9 µm 4% w/v), 100 µl of 20× phosphate buffered saline are added and 2 ml of anti-ABO01 antibody (91 13 D10 Diagast clone) or anti-ABO02 antibody (96 21 A8 Diagast clone) are dissolved. The volume is completed up to 4 ml with demineralized water. The solution is end over end mixed overnight to ensure coupling.

The excess active groups are blocked by suspending in the bead antibody solution 150 µl of 1M ethanolamine and mixed for 2 hours at room temperature. The coupled beads are then washed extensively 2 times with 3 ml of conservation buffer (centrifugation 5 min at 2500 g before and after washes). Finally the bead pellet is resuspended in the conservation buffer to get back the introduced bead solution weight.

2. Reaction Device Preparation and Detection Procedure

The device is a moulded plastic cassette in which a Porex HDPE hydrophobic membrane of 0.6 mm thickness and porosity between 9 to 12 µm, a draining pad (cotton wool from Alan&co) and an absorbent pad (Cleanis) are assembled.

The porous membrane is hydrophilized with 1 µl of a surfactant solution (phosphate buffered saline supplemented with 1% Triton X-100 and 1% of green dye). 10 µl of antibody coupled beads at 3%, are then spotted. The device is dried for 15 min at 37° C., 20% humidity before use.

The detection procedure is initiated by introducing in each well 50 µl of red blood cells diluted at 0.15% in Chromasolcoombs supplemented with 0.00625% Tween20.

Mixed field A and B populations are generated by mixing respectively A and O or B and O red blood cells pre diluted at 0.15% in Chromasolcoombs at desired concentrations (30% O with 70% A or B red blood cells or 50% O with 50% A or B red blood cells).

A first image before washes is acquired. The reaction zone is then washed twice with 30 µl of phosphate buffered saline supplemented with 0.2% Tween-20. An image is acquired after each wash.

3. Results

Figure 12:
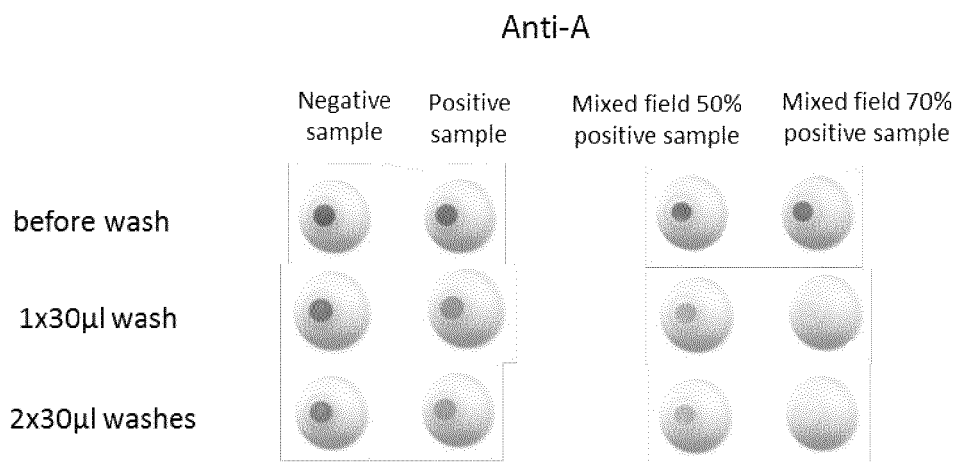
FIG. 12: a. and c. Detection of red blood cell ABO01 or ABO02 antigens by IgM antibody (anti-ABO01 and anti-ABO02) coupled to aldehyde/sulfate 9 µm latex beads. b. and d. Signal interpretation allowing discrimination of mixed field populations.
Figure 12:
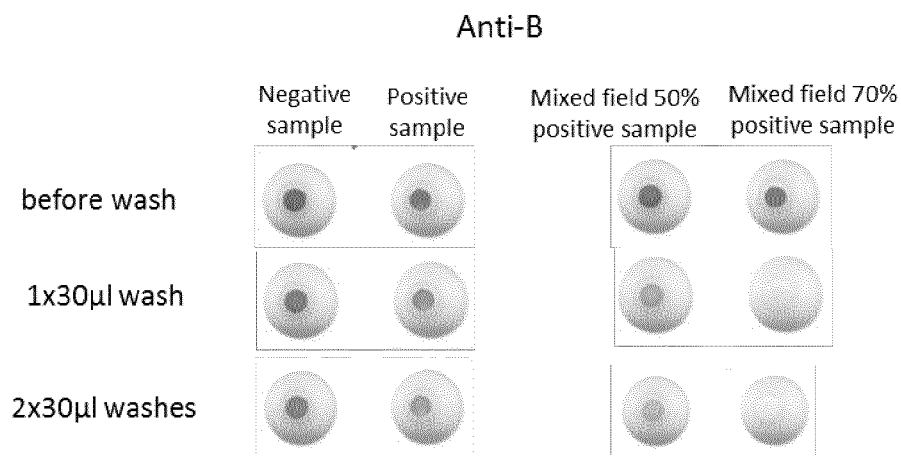

As shown on FIGS. 12a and c, before washes, all the spots appear in dark gray (or in red). Specificity is reached after the second wash: the presence of a red spot (visible as a dark gray spot) indicates an immune complex formation, and therefore a positive reaction, while the presence of a colourless spot reflects a negative reaction.

FIGS. 12b and d shows that the discrimination between native and mixed field populations is met after intensity interpretation of the acquired images (the signal before and after two washes is subtracted).

Example 9: Detection of Weak RH1 Antigens and Extended Phenotyping With Indirect Coupling of Red Blood Cells Antibodies to Beads Via Affinity Proteins for Antibodies 1. Protein AGL Coupling On 1 ml of homogenized 4% beads, 50 µg of Protein AGL are dissolved in 3 ml PBS1× and are added. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

2. Reaction Device Preparation and Detection Procedure

The device is a moulded plastic cassette in which a Porex HDPE hydrophobic membrane of 0.6 mm thickness and porosity between 9 to 12 µm, a draining pad (9610HY) and an absorbent pad (Cleanis) are assembled.

The porous membrane is hydrophilized with 1 µl of a surfactant solution with AGL coupled beads (1.5% Triton X-100; phosphate buffered saline supplemented with 0.5% bovine serum albumin; 0.25M saccharose and 5.1% beads). The device is dried for 15 min at 37° C., 20% humidity before use.

The detection procedure is initiated by introducing in each well 50 µl of reactive (Weak RH1 or Extended phenotyping); add 50 µl of red blood cells diluted at 1.5% in PBS1× supplemented with 0.00625% Tween20.

A first image before washes is acquired. The reaction zone is then washed with 30 µl of phosphate buffered saline supplemented with 0.2% Tween-20. An image is acquired after wash.

3 Results

Figure 13:
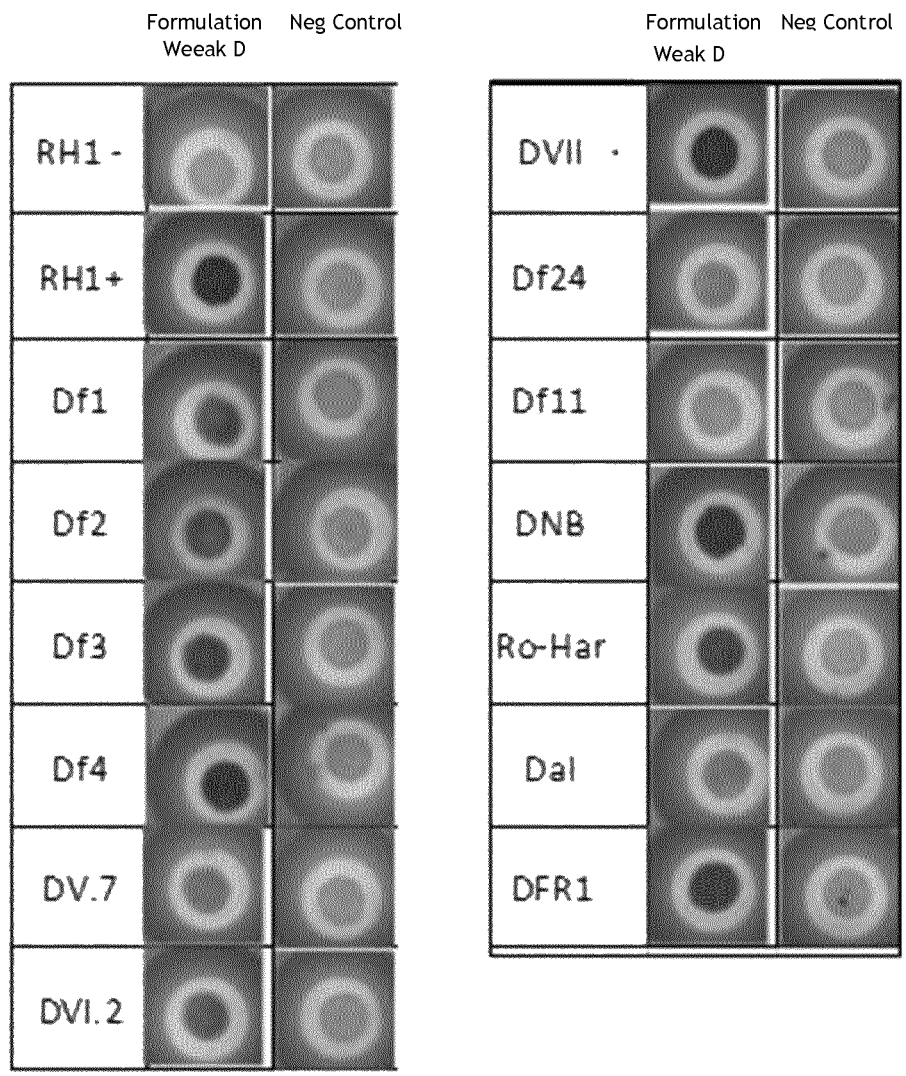
FIG. 13: a. Detection of weak RH1 antigens: different types of weak RH1 red blood cells (Df1, Df2, . . . ) are captured by anti-RH1 (HM16 and ESD1 clones) fixed to A/G/L protein coupled to aldehyde/sulfate 9 µm latex beads. b. Detection of antigens of Duffy (FY1 and FY2), KIDD (JK1 and JK2) and MSN (MNS3 and MNS4 systems): positive red blood cells are captured by specific antibodies fixed to A/G/L protein coupled to aldehyde/sulfate 9 µm latex beads.

FIG. 13a shows the weak RH1 resulting image on which is observed the presence of dark grey spots (corresponding to the red spot in color image) indicating an immune complex formation and therefore a positive reaction, while the presence of a colorless spot reflects a negative reaction.

FIG. 13b shows the extending phenotyping resulting image on which is observed the presence of dark grey spots (corresponding to the red spot in color image) indicating an immune complex formation and therefore a positive reaction, while the presence of a colorless spot reflects a negative reaction.

Example 10: Reverse Grouping Via 6D4 Antibody Coupled to Beads

1. Reverse Grouping 1.1. Antibodies Coupling

On 1 ml of homogenized 4% beads (Thermo Fisher latex Aldehyde/Sulfate 9 µm 4% w/v), 3 ml of 1× phosphate buffered saline are added and 100 µg of CP6D4 antibody are dissolved. The solution is end over end mixed overnight to ensure coupling.

The excess active groups are blocked by suspending in the bead antibody solution 150 µl of 1M ethanolamine and mixed for 2 hours at room temperature. The coupled beads are then washed extensively 2 times with 3 ml of conservation buffer (centrifugation 5 min at 2500 g before and after washes). Finally the bead pellet is resuspended in the conservation buffer to get back the introduced bead solution weight.

1.2. Reaction Device Preparation And Detection Procedure

The device is a moulded plastic cassette in which a Porex HDPE hydrophobic membrane of 0.6 mm thickness and porosity between 9 to 12 µm, a draining pad (Subrenat 9610 HY) and an absorbent pad (Cleanis) are assembled.

The porous membrane is hydrophilized with 0.5 µl of a surfactant solution (phosphate buffered saline supplemented with 1.5% Triton X-100; 0.5% green dye). 5 µl of antibody coupled beads at 1% are spotted and the device is dried 15 min at 37° C., 10% humidity before immediate use or extended conservation.

A test is initiated by incubating 30 µl of plasma and 20 µl red blood cells (A1; B; A2; O) during 5 min. 25 µl are introduced in each well followed by a 30 µl of wash buffer (phosphate buffered saline supplemented with 0.2% Tween20).

1.3. Results

Figure 14:
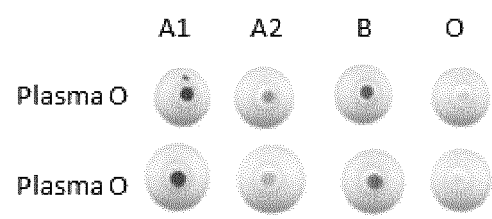
FIG. 14: Reverse grouping, test red blood cells of known phenotype (A1, A2, B and O) are incubated with plasma and captured by anti-Human IgM (CP6D4 clones) coupled to aldehyde/sulfate 9 µm latex beads.

FIG. 14 shows the presence of dark gray spots (corresponding to red spots) which indicate a capture of IgM sensitized red blood cells, and therefore a positive reverse grouping reaction, while the presence of a colorless spot reflects a negative reaction (non-sensitized red blood cells).

Example 11: DAT (Direct Coombs Test) Test Using the Device of the Invention

1. Red Blood Cell Pre Sensitized With Antibodies 1.1. Antibodies Coupling

On 3 ml of homogenized 4% beads (Thermo Fisher latex Aldehyde/Sulfate 9 µm 4% w/v), a 3 ml solution of anti-human globulin is dissolved. The AHG studied are SA6532 (polyclonal rabbit antibodies directed against human IgGs), C5-1 (Diagast clone, mouse IgG directed against human IgGs) and 188 33 (Diagast clone, mouse IgM directed against human IgGs). The solution is end over end mixed one hour to ensure coupling.

The bead suspension is centrifuged 5 min at 2500 g. The excess active groups are blocked by resuspending the bead pellet in 6 ml of an ethanolamine solution at 50 mM, followed by a 30 min mixing. The coupled beads are then washed extensively 2 times with 9 ml of conservation buffer (centrifugation 5 min at 2500 g before and after washes). Finally the bead pellet is resuspended in the conservation buffer to get back the introduced bead solution weight.

1.2. Reaction Device Preparation and Detection Procedure

The device is a moulded plastic cassette in which a Porex HDPE hydrophobic membrane of 0.6 mm thickness and porosity between 9 to 12 µm, a draining pad (Subrenat 9610 HY) and an absorbent pad (Cleanis) are assembled.

The porous membrane is hydrophilized with 0.5 µl of a surfactant solution (phosphate buffered saline supplemented with 1.5% Triton X-100; 0.5% green dye). 5 µl of antibody coupled beads at 3% are spotted and the device is dried 15 min at 37° C., 10% humidity before immediate use or extended conservation.

Red blood cells are in vitro pre sensitized with FY, KEL1KEL1 or RH1 IgG antibodies to simulate direct coombs positive red blood cells.

A test is initiated by diluting red blood cells (coombs negative or positive) at 0.25% in chromasolcoombs (Diagast formulation) supplemented with 0.00625% Tween20. 50 µl are introduced in each well followed by a 30 µl of wash buffer (phosphate buffered saline supplemented with 0.2% Tween20).

2. Direct Antiglobulin Test With Anti-IgG and Anti-C3d 2.1. Antibodies Coupling

On 1 ml of homogenized 4% beads (Thermo Fisher latex Aldehyde/Sulfate 9 µm 4% w/v), 3 ml of 1× phosphate buffered saline are added and 100 µg of SA6532 or C7610 antibody are dissolved. The solution is end over end mixed overnight to ensure coupling. The coupled beads are then centrifuged 5 min at 2500 g. Finally the bead pellet is resuspended in the conservation buffer to get back the introduced bead solution weight.

2.2. Reaction Device Preparation and Detection Procedure

The device is a moulded plastic cassette in which a Porex HDPE hydrophobic membrane of 0.6 mm thickness and porosity between 9 to 12 µm, a draining pad (Subrenat 9610 HY) and an absorbent pad (Cleanis) are assembled.

The porous membrane is hydrophilized with 0.5 µl of a surfactant solution (phosphate buffered saline supplemented with 1.5% Triton X-100; 0.5% green dye). 5 µl of antibody coupled beads at 4% are spotted and the device is dried 15 min at 37° C., 10% humidity before immediate use or extended conservation.

A test is initiated by diluting red blood cells (DAT negative or positive) at 1.5% in phosphate buffered saline supplemented with 0.00625% Tween20. 50 µl are introduced in each well followed by a 30 µl of wash buffer (phosphate buffered saline supplemented with 0.2% Tween20).

3. DAT Via Affinity Proteins for Antibodies 3.1. Protein AGL Coupling

On 1 ml of homogenized 4% beads, 50 µg of Protein AGL are dissolved in 3 ml PBS1× and are added. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

3.2. Reaction Device Preparation And Detection Procedure

The device is a moulded plastic cassette in which a Porex HDPE hydrophobic membrane of 0.6 mm thickness and porosity between 9 to 12 µm, a draining pad (9610HY) and an absorbent pad (Cleanis) are assembled.

The porous membrane is hydrophilized with 1 µl of a surfactant solution with AGL coupled beads (1.5% Triton X-100; phosphate buffered saline supplemented with 0.5% bovine serum albumin; 0.25M saccharose and 5.1% beads). The device is dried for 15 min at 37° C., 20% humidity before use.

The detection procedure is initiated by incubation in well 20 µl of reactive (DAT); add 50 µl of red blood cells diluted at 3% in PBS1× supplemented with 0.00625% Tween20 in well; add 20 µl IAT solution 2 buffer. Transfer 120 µl of mix in cartridge well.

A first image before washes is acquired. The reaction zone is then washed with 40 µl of IAT solution 2 buffer. An image is acquired after wash.

4. Results

Figure 15:
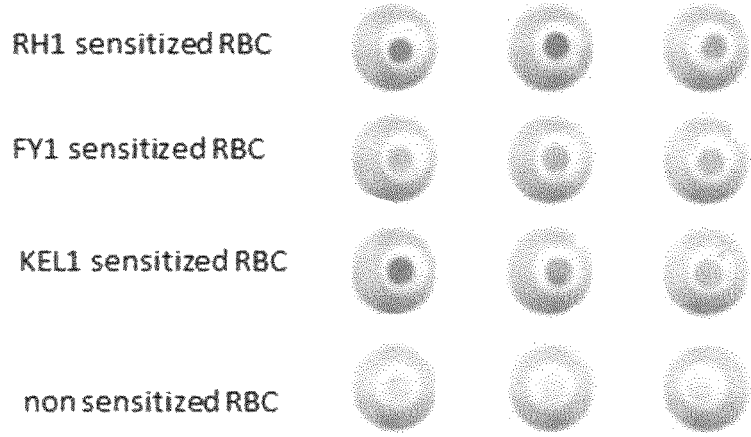
FIG. 15: Direct coombs test: a. IgG sensitized red blood cells are captured by anti-Human globulins (SA6532, CPC5-1 and 188 33 clones) coupled to aldehyde/sulfate 9 µm latex beads. b. Positive red blood cells are captured by an anti-Human globulin (SA6532) and/or an anti-human C3d (C7610) coupled to aldehyde/sulfate 9 µm latex beads. c. Positive red blood cells are fixed to an anti-human globulin (SA6532) and/or an Anti-Human C3d (C7610) and captured on A/G/L protein coupled to aldehyde/sulfate 9 µm latex beads.
Figure 15:
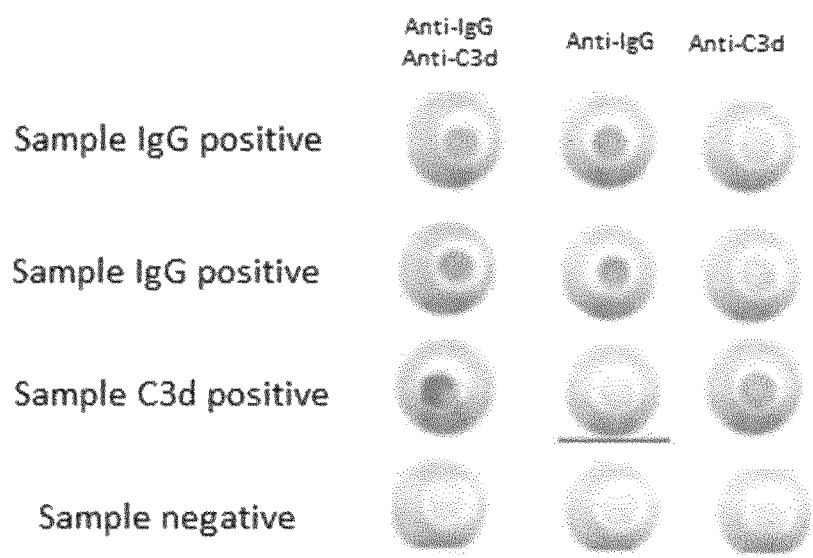

FIG. 15a shows the presence of dark gray spots (corresponding to red spots) which indicate a capture of IgG sensitized red blood cells, and therefore a positive direct coombs reaction, while the presence of a colourless spot reflects a negative reaction (non-sensitized red blood cells).

FIG. 15b shows the presence of dark gray spots (corresponding to red spots) which indicate a capture of IgG or/and C3D sensitized red blood cells, and therefore a positive reaction, while the presence of a colorless spot reflects a negative reaction (non-sensitized red blood cells).

FIG. 15c shows the resulting image on which is observed the presence of dark grey spots (corresponding to the red spot in color image) indicating an immune complex formation and therefore a positive reaction, while the presence of a colorless spot reflects a negative reaction.

Example 12: Detection of Antibodies Specific for Malaria Antigen Using the Device of Invention 1. Antigen Coupling On 1 ml of homogenized 4% beads, 100 μg of Antigen Mal003 are dissolved in 3 ml PBS1× and are added. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

2. Antibodies Coupling for Detection

On 1 ml of homogenized 4% beads 1 μm, 200 μg of Antibodies 6D4 are dissolved in 3 ml PBS1× and are added. The solution is end over end mixed overnight to ensure coupling.

The coupled beads are then centrifuged 5 min at 5000 g. Finally the bead pellet is resuspended in the conservation buffer (phosphate buffered saline supplemented with 0.5% bovine serum albumin and 0.25M saccharose) to get back the introduced bead solution weight.

3. Reaction Device Preparation and Detection Procedure With HRP

The device is a moulded plastic cassette in which a Porex HDPE hydrophobic membrane of 0.6 mm thickness and porosity between 9 to 12 μm, a draining pad (9610HY) and an absorbent pad (Cleanis) are assembled.

The porous membrane is hydrophilized with 0.5 μl of a surfactant solution (phosphate buffered saline supplemented with 2% Triton X-100 and 1% of green dye). 2 μl of antigen Mal003 coupled beads at 4%, are then spotted. The device is dried for 15 min at 37° C., 20% humidity before use.

The detection procedure is initiated by introducing in each well 100 μl of sample (kit ab178649). Add 100 μl of antibody Anti-IgG and/or Anti-IgM HRP conjugate (kit ab178649). A first image before washes is acquired. The reaction zone is then washed with 30 μl of phosphate buffered saline supplemented with 0.2% Tween-20. The reaction zone is then washed with 30 μl of revelation buffer (TMB Substrate (kit ab178649)). An image is acquired after 15 min.

4. Reaction Device Preparation and Detection Procedure With Beads

The device is a moulded plastic cassette in which a Porex HDPE hydrophobic membrane of 0.6 mm thickness and porosity between 9 to 12 μm, a draining pad (9610HY) and an absorbent pad (Cleanis) are assembled.

The porous membrane is hydrophilized with 0.5 μl of a surfactant solution (phosphate buffered saline supplemented with 2% Triton X-100 and 1% of green dye). 2 μl of antigen Mal003 coupled beads at 4%, are then spotted. The device is dried for 15 min at 37° C., 20% humidity before use.

The detection procedure is initiated by introducing in each well 100 μl of sample (Kit ab178649). Add 30 μl of antibody 6D4 beads 1 μm at 0.1%. A first image before washes is acquired. The reaction zone is then washed with 120 μl of phosphate buffered saline supplemented with 0.2% Tween-20. An image is acquired after wash.

5. Reaction Device Preparation and Detection Procedure With Colloidal Gold Nanoparticles The device is a moulded plastic cassette in which a Porex HDPE hydrophobic membrane of 0.6 mm thickness and porosity between 9 to 12 μm, a draining pad (9610HY) and an absorbent pad (Cleanis) are assembled.

The porous membrane is hydrophilized with 0.5 μl of a surfactant solution (phosphate buffered saline supplemented with 2% Triton X-100 and 1% of green dye). 5 μl of antigen Mal003 coupled beads at 4%, are then spotted. The device is dried for 15 min at 37° C., 20% humidity before use.

The detection procedure is initiated by introducing in each well 50 μl of sample (Kit ab178649). Add 10 μl of Anti-Human IgA, IgG, IgM 60 nm gold conjugate (AC-60-14-10). A first image before washes is acquired. The reaction zone is then washed with 50 μl of phosphate buffered saline supplemented with 0.2% Tween-20. An image is acquired after wash.

6. Results

Figure 16:
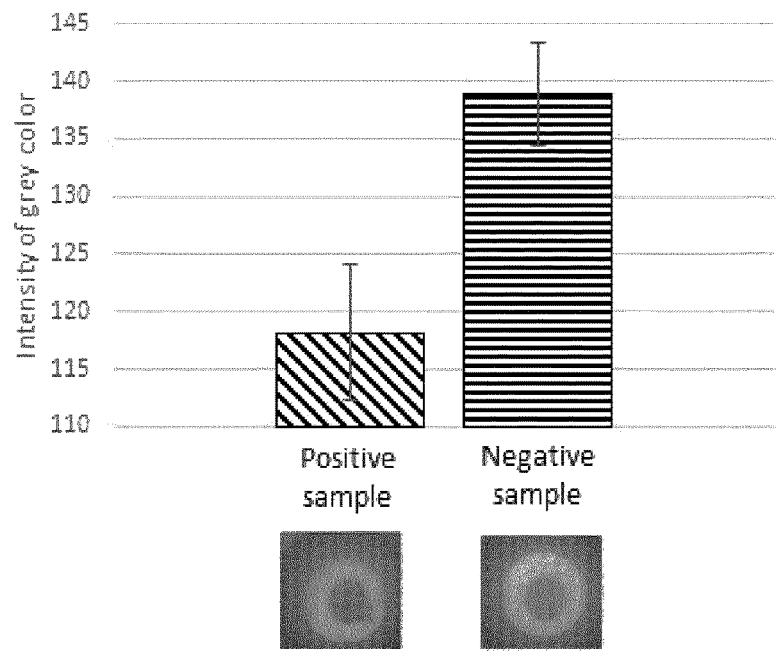
FIG. 16: Detection of antibodies specific for *Plasmodium falciparum* MSP1 antigen. a. using the device of invention with HRP detection method b. using the device of the invention with 1 µm red colored beads as detection method. c. using the device of the invention with colloidal gold nanoparticles as detection method. For each example, a negative and a positive reaction are shown as well as the quantification of the signal intensity (n=3-5).
Figure 16:
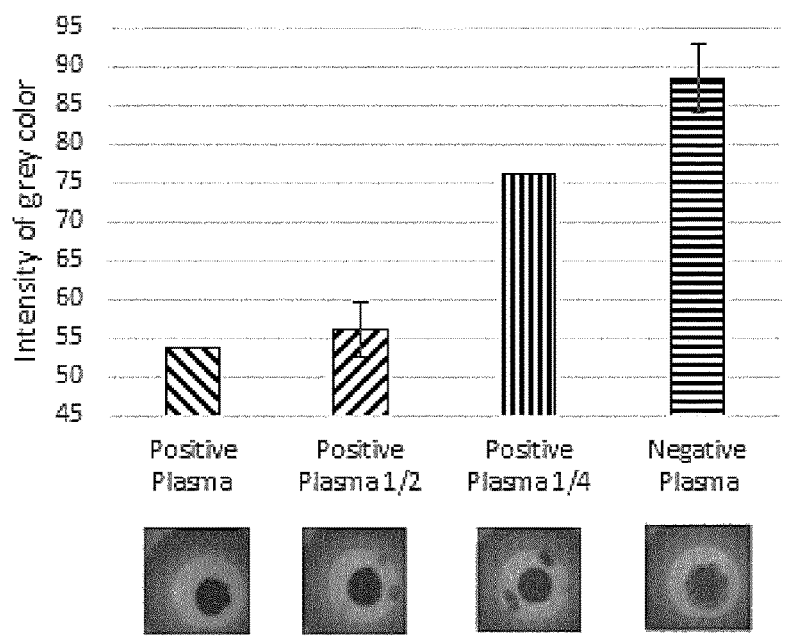

FIG. 16a shows the resulting image on which is observed the presence of dark grey spots indicating an immune complex formation and therefore a positive reaction, while the presence of a colorless spot reflects a negative reaction and graphic with intensity of grey color.

FIG. 16b shows the resulting image on which is observed the presence of dark grey spots indicating an immune complex formation and therefore a positive reaction, while the presence of a colorless spot reflects a negative reaction and graphic with intensity of grey color.

FIG. 16c shows the resulting image on which is observed the presence of dark grey spots indicating an immune complex formation and therefore a positive reaction, while the presence of a colorless spot reflects a negative reaction and graphic with intensity of grey color.

Example 13: Detection of Antibodies Specific for *T. Pallidum* Antigens Using the Device of Invention With 1 μm-Red Colored Beads as Detection Method 1. Antigen Coupling On 1 ml of homogenized 4% beads, 100 μg of p15, p17, p47 *T. Pallidum antigens* (30-AT76) are dissolved in 3 ml PBS1× and are added. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

2. Antibodies Coupling for Detection

On 1 ml of homogenized 4% beads 1 μm, 200 μg of AGL protein are dissolved in 3 ml PBS1× and are added. The solution is end over end mixed overnight to ensure coupling.

The coupled beads are then centrifuged 5 min at 5000 g. Finally the bead pellet is resuspended in the conservation buffer (phosphate buffered saline supplemented with 0.5% bovine serum albumin and 0.25M saccharose) to get back the introduced bead solution weight.

3. Reaction Device Preparation and Detection Procedure

The device is a moulded plastic cassette in which a Porex HDPE hydrophobic membrane of 0.6 mm thickness and porosity between 9 to 12 µm, a draining pad (9610HY) and an absorbent pad (Cleanis) are assembled.

The porous membrane is hydrophilized with 0.5 µl of a surfactant solution (phosphate buffered saline supplemented with 2% Triton X-100 and 1% of green dye). 2 µl of p15, p17, p47 *T. Pallidum* antigen coupled beads at 4%, are then spotted. The device is dried for 15 min at 37° C., 20% humidity before use.

The detection procedure is initiated by introducing in each well 10 µl of sample (*Treponema pallidum* antibody 20-TR89). Add 30 µl of AGL protein beads 1 µm at 0.1%. A first image before washes is acquired. The reaction zone is then washed with 120 µl of phosphate buffered saline supplemented with 0.2% Tween-20. An image is acquired after wash.

4. Results

Figure 17:
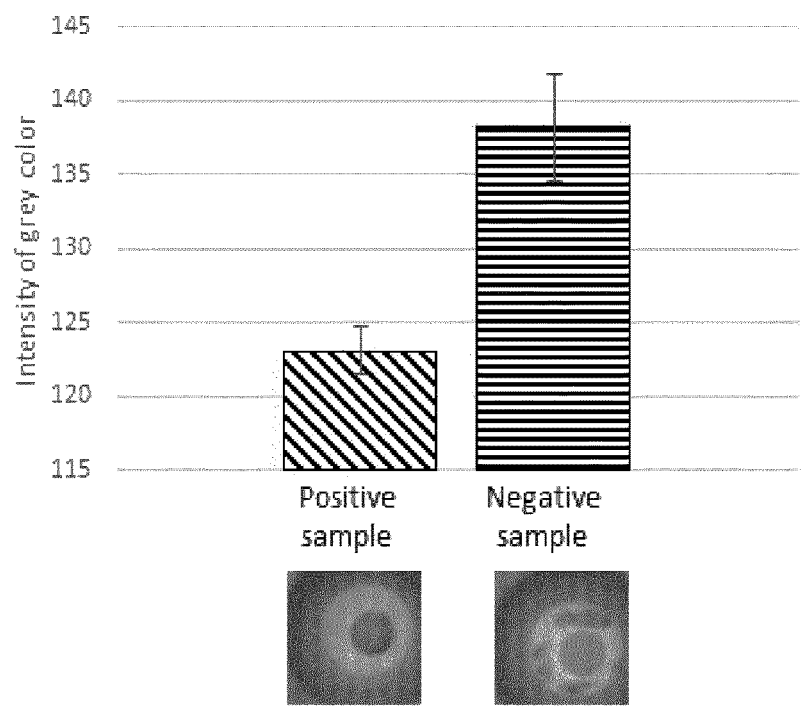
FIG. 17. Detection of antibodies specific for *Treponema pallidum* p15, p17 and p47 antigens using the device of invention with 1 μm red-colored beads as detection method. A negative and a positive reaction are shown as well as the quantification of the signal intensity (n=3).
Figure 17:
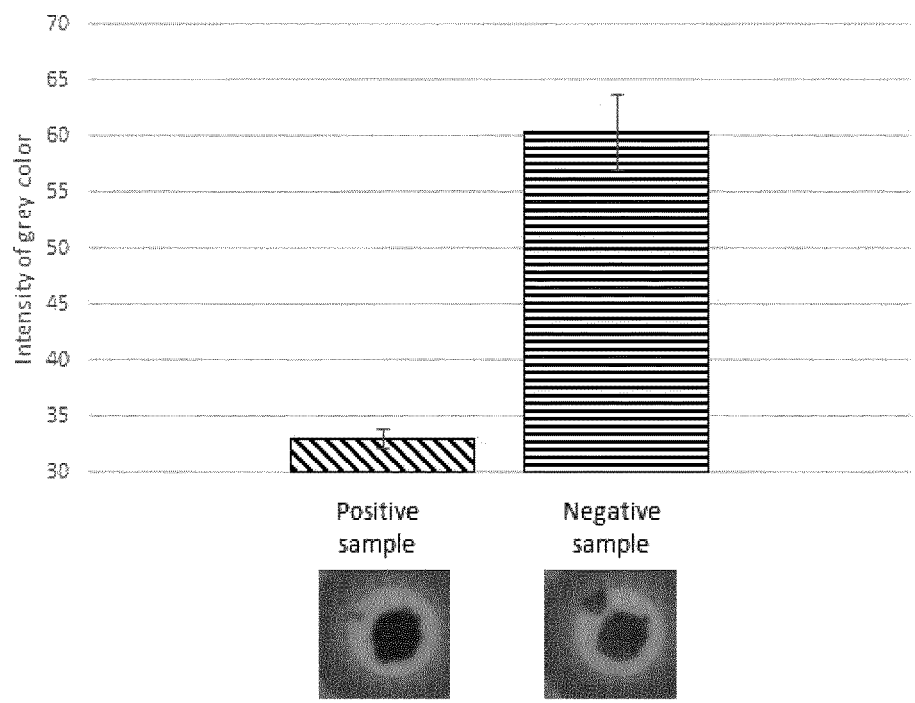

FIG. 17 shows the resulting image on which is observed the presence of dark grey spots indicating an immune complex formation and therefore a positive reaction, while the presence of a colorless spot reflects a negative reaction and graphic with intensity of grey color.

Example 14: Detection of Antibodies Specific for Hepatitis B Virus Antigen (HbsAg) Using the Device of Invention with Beads 1 µm Red Detection Method

1. Antigen Coupling

On 1 ml of homogenized 4% beads, 100 µg of HBs Antigen (30-AH15) are dissolved in 3 ml PBS1× and are added. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

2. Antibodies Coupling For Detection

On 1 ml of homogenized 4% beads 1 µm, 200 µg of AGL protein are dissolved in 3 ml PBS1×and are added. The solution is end over end mixed overnight to ensure coupling.

The coupled beads are then centrifuged 5 min at 5000 g. Finally the bead pellet is resuspended in the conservation buffer (phosphate buffered saline supplemented with 0.5% bovine serum albumin and 0.25M saccharose) to get back the introduced bead solution weight.

3. Reaction Device Preparation and Detection Procedure

The device is a moulded plastic cassette in which a Porex HDPE hydrophobic membrane of 0.6 mm thickness and porosity between 9 to 12 µm, a draining pad (9610HY) and an absorbent pad (Cleanis) are assembled.

The porous membrane is hydrophilized with 0.5 µl of a surfactant solution (phosphate buffered saline supplemented with 2% Triton X-100 and 1% of green dye). 2 µl of HBs antigen coupled beads at 4%, are then spotted. The device is dried for 15 min at 37° C., 20% humidity before use.

The detection procedure is initiated by introducing in each well 10 µl of sample (HBsAg antibody 10-H05G). Add 30 µl of AGL protein beads 1 µm at 0.1%. A first image before washes is acquired. The reaction zone is then washed with 120 µl of phosphate buffered saline supplemented with 0.2% Tween-20. An image is acquired after wash.

4. Results

Figure 18:
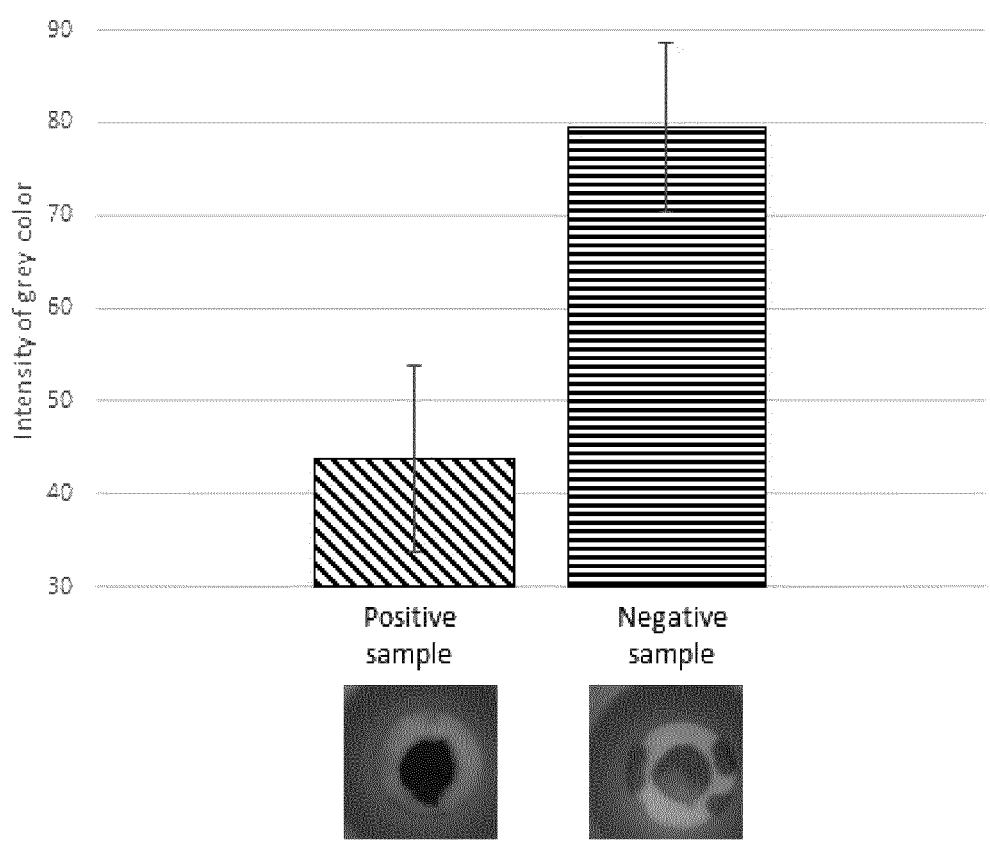
FIG. 18. Detection of antibodies specific for HBsAg antigen from hepatitis B virus using the device of invention with 1 μm red-colored beads as detection method. A negative and a positive reaction are shown as well as the quantification of the signal intensity (n=3).

FIG. 18 shows the resulting image on which is observed the presence of dark grey spots indicating an immune complex formation and therefore a positive reaction, while the presence of a colorless spot reflects a negative reaction and graphic with intensity of grey color.

Example 15: Detection of the Hepatitis B Virus Antigen Using the Device of Invention

1. Antigen Coupling

On 1 ml of homogenized 4% beads, 100 µg of HBs Antibody (10-H05G) are dissolved in 3 ml PBS1× and are added. The solution is end over end mixed overnight to ensure coupling.

The coupled beads are then centrifuged 5 min at 2500 g. Finally the bead pellet is resuspended in the conservation buffer (phosphate buffered saline supplemented with 0.5% bovine serum albumin and 0.25M saccharose) to get back the introduced bead solution weight.

2. Antibodies Coupling For Detection

On 1 ml of homogenized 4% beads 1 µm, 200 µg of HBs Antibody (10-H05H) are dissolved in 3 ml PBS1× and are added. The solution is end over end mixed overnight to ensure coupling.

The coupled beads are then centrifuged 5 min at 5000 g. Finally the bead pellet is resuspended in the conservation buffer (phosphate buffered saline supplemented with 0.5% bovine serum albumin and 0.25M saccharose) to get back the introduced bead solution weight.

3. Reaction Device Preparation and Detection Procedure With HRP Method as Detection Method The device is a moulded plastic cassette in which a Porex HDPE hydrophobic membrane of 0.6 mm thickness and porosity between 9 to 12 µm, a draining pad (9610HY) and an absorbent pad (Cleanis) are assembled.

The porous membrane is hydrophilized with 0.5 µl of a surfactant solution (phosphate buffered saline supplemented with 2% Triton X-100 and 1% of green dye). 2 µl of antigen HBs Antibody (10-H05G) coupled beads at 4%, are then spotted. The device is dried for 15 min at 37° C., 20% humidity before use.

The detection procedure is initiated by introducing in each well 50 µl of sample (kit 1701-12). Add 50 µl of antibody Anti-HBs antigen HRP conjugate (kit 1701-12). A first image before washes is acquired. The reaction zone is then washed with 100 µl of revelation buffer (TMB Substrate (kit 1701-12)). An image is acquired after 15 min.

4. Reaction Device Preparation and Detection Procedure With Beads Method

The device is a moulded plastic cassette in which a Porex HDPE hydrophobic membrane of 0.6 mm thickness and porosity between 9 to 12 µm, a draining pad (9610HY) and an absorbent pad (Cleanis) are assembled.

The porous membrane is hydrophilized with 0.5 µl of a surfactant solution (phosphate buffered saline supplemented with 2% Triton X-100 and 1% of green dye). 2 µl of HBs Antibody (10-H05G) coupled beads at 4%, are then spotted. The device is dried for 15 min at 37° C., 20% humidity before use.

The detection procedure is initiated by introducing in each well 10 µl of sample HBs antigen (kit 1701-12). Add 100 µl of HBs Antibody (10-H05H) beads 1 µm at 0.025%. A first image before washes is acquired. The reaction zone is then washed with 120 µl of phosphate buffered saline supplemented with 0.2% Tween-20. An image is acquired after wash.

5. Results

Figure 19:
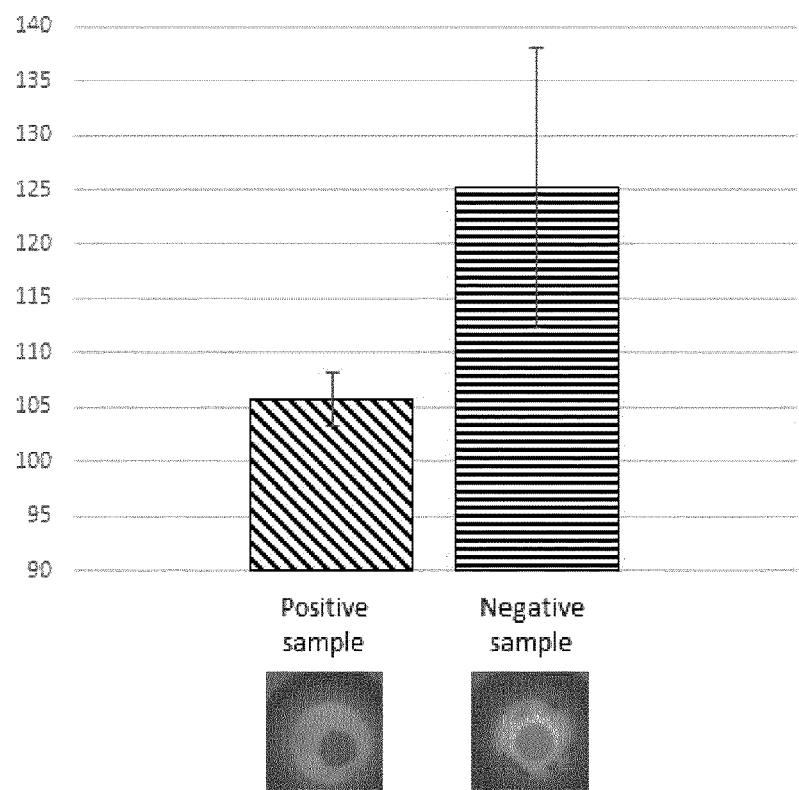
FIG. 19. Detection of HBsAg antigen from hepatitis B virus. a. using the device of invention with HRP (Horseradish peroxidase) as detection method (graphic and image). b. using the device of invention with 1 μm red-colored beads as detection method. For each example, a negative and a positive reaction are shown as well as the quantification of the signal intensity (n=3).
Figure 19:
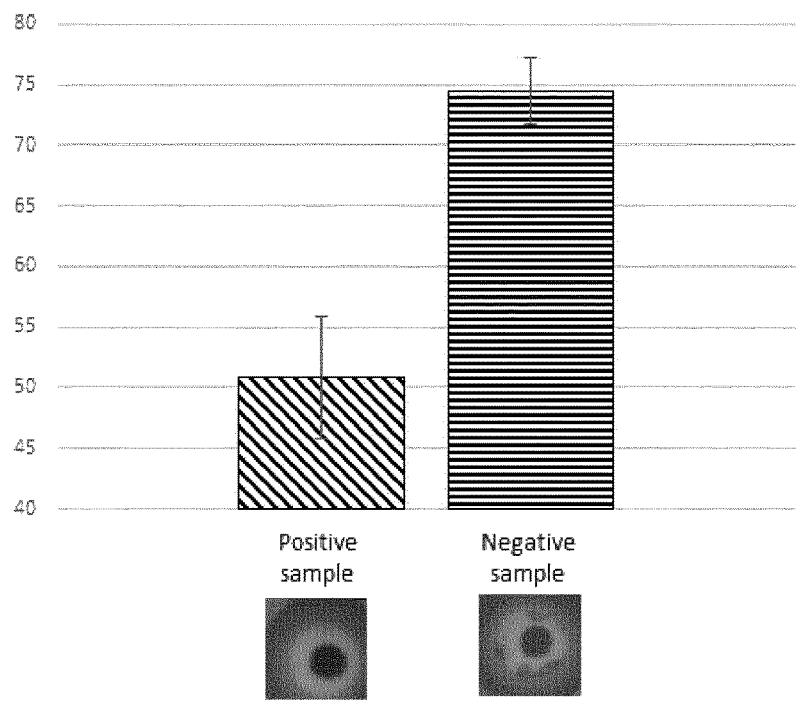

FIG. 19a shows the resulting image on which is observed the presence of dark grey spots indicating an immune complex formation and therefore a positive reaction, while the presence of a colorless spot reflects a negative reaction and graphic with intensity of grey color.

FIG. 19b shows the resulting image on which is observed the presence of dark grey spots indicating an immune complex formation and therefore a positive reaction, while the presence of a colorless spot reflects a negative reaction and graphic with intensity of grey color.

The invention claimed is:

1. An in vitro diagnosis device for detecting and/or identifying an antigen and/or antibody, from a sample of biological fluid comprising:
   a support, and
   a hydrophobic porous membrane arranged in said support comprising at least one hydrophilic reaction area intended to receive said sample, wherein on said hydrophilic reaction area, which is a surface smaller than the hydrophobic porous membrane, are deposited beads, and wherein at least one antibody or antigen is fixed on said beads.

2. The in vitro diagnosis device of claim 1, wherein the antibody is selected from the group consisting of anti-red blood cell antibodies, antiplatelet antibodies, antibodies of viral antigens, antibodies of bacterial antigens, and antibodies of parasite antigens.

3. The in vitro diagnosis device of claim 1, wherein the antigen is selected from the group consisting of red blood cells antigens, platelet antigens, viral antigens, bacterial antigens, and parasite antigens.

4. The in vitro diagnosis device of claim 1, wherein the antibody is an antibody of viral antigens and the antigen is a viral antigen of the hepatitis B virus or the hepatitis C virus.

5. The in vitro diagnosis device of claim 1, wherein the antibody is an antibody of bacterial antigens and the antigen is a bacterial antigen of the genus *Treponema*.

6. The in vitro diagnosis device of claim 1, wherein the antibody is an antibody of parasite antigens and the antigen is a parasite antigen of the genus *Plasmodium*.

7. The in vitro diagnosis device according to claim 1, wherein said antibody or antigen is directly or indirectly fixed on said beads.

8. The in vitro diagnosis device according to claim 1, wherein said antibody or antigen is indirectly fixed on said beads via another antibody.

9. The in vitro diagnosis device according to claim 1, wherein said antibody is indirectly fixed on said beads via a ligand selected from proteins with affinity for antibodies protein A, protein G, or protein L.

10. The in vitro diagnosis device according to claim 1, wherein said bead surface comprises at least one chemical group selected from aldehyde groups, chloromethyl group, NHS groups, and carboxyl groups.

11. The in vitro diagnosis device according to claim 1, wherein the mean size of said beads is between 1 µm and 130 µm.

12. The in vitro diagnosis device according to claim 1, wherein said beads are used at concentration between 1% and 10% of the solution in which said beads are suspended and wherein the deposited volume of said solution is between 1 and 100 µl.

13. The in vitro diagnosis device according to claim 1, wherein the thickness of the hydrophobic porous membrane is between 0.4 mm and 2 mm.

14. The in vitro diagnosis device according to claim 1, said device also comprising at least one layer, which is an absorbent layer, arranged underneath the hydrophobic porous membrane.

15. The in vitro diagnosis device according to claim 1, which further comprises a draining layer arranged between the hydrophobic porous membrane and the absorbent layer.

* * * * *